US009308161B2

(12) United States Patent
Bouez et al.

(10) Patent No.: US 9,308,161 B2
(45) Date of Patent: Apr. 12, 2016

(54) SUBSTANCE FOR RESTORING NORMAL CO-EXPRESSION AND INTERACTION BETWEEN THE LOX AND NRAGE PROTEINS

(75) Inventors: Charbel Bouez, Lyons (FR); Claudine Gleyzal, Lyons (FR); Isabelle Orly, Irigny (FR); Valerie Andre, Ludwigshafen (DE); Pascal Sommer, Saint Genis Laval (FR); Corinne Reymermier, Charly (FR); Odile Damour, Saint Genis Laval (FR); Eric Perrier, Les Cotes d'arey (FR)

(73) Assignees: BASF Beauty Care Solutions France S.A.S., Lyons (FR); Centre National De La Recherche Scientifique, Paris (FR); Université Claude Bernard Lyon 1, Villeurbanne (FR)

( * ) Notice: Subject to any disclaimer, the term of this patent is extended or adjusted under 35 U.S.C. 154(b) by 15 days.

(21) Appl. No.: 13/455,366

(22) Filed: Apr. 25, 2012

(65) Prior Publication Data

US 2012/0225141 A1 Sep. 6, 2012

Related U.S. Application Data

(62) Division of application No. 12/091,768, filed as application No. PCT/FR2006/051117 on Oct. 26, 2006, now abandoned.

(30) Foreign Application Priority Data

Oct. 28, 2005 (FR) ...................................... 05 11112

(51) Int. Cl.
| | |
|---|---|
| A61K 36/00 | (2006.01) |
| A61K 8/97 | (2006.01) |
| A61K 36/17 | (2006.01) |
| A61K 36/185 | (2006.01) |
| A61K 36/48 | (2006.01) |
| A61K 36/54 | (2006.01) |
| A61Q 19/00 | (2006.01) |
| A61Q 19/08 | (2006.01) |
| G01N 33/50 | (2006.01) |

(52) U.S. Cl.
CPC . *A61K 8/97* (2013.01); *A61K 36/17* (2013.01); *A61K 36/185* (2013.01); *A61K 36/48* (2013.01); *A61K 36/54* (2013.01); *A61Q 19/00* (2013.01); *A61Q 19/004* (2013.01); *A61Q 19/08* (2013.01); *G01N 33/5011* (2013.01)

(58) Field of Classification Search
None
See application file for complete search history.

(56) References Cited

U.S. PATENT DOCUMENTS

| | | | |
|---|---|---|---|
| 4,526,793 A | 7/1985 | Ingenbleek et al. | |
| 5,676,948 A | 10/1997 | Bonte et al. | |
| 6,989,150 B1 | 1/2006 | Golz-Berner et al. | |
| 8,293,291 B2 | 10/2012 | Smith | |
| 8,568,794 B2 | 10/2013 | Diehl et al. | |
| 2003/0086949 A1 | 5/2003 | Perrier et al. | |
| 2003/0152597 A1 | 8/2003 | Liviero et al. | |
| 2003/0170199 A1* | 9/2003 | Leclere | 424/74 |
| 2004/0043083 A1 | 3/2004 | Ryu et al. | |
| 2004/0044077 A1 | 3/2004 | Katagiri et al. | |
| 2004/0071791 A1 | 4/2004 | Tang | |
| 2004/0096925 A1 | 5/2004 | Perrier et al. | |
| 2004/0115286 A1 | 6/2004 | Lee et al. | |
| 2004/0185122 A1 | 9/2004 | Obukowicz et al. | |
| 2005/0025846 A1 | 2/2005 | Brown et al. | |
| 2005/0031572 A1 | 2/2005 | Gallinat et al. | |
| 2005/0181080 A1 | 8/2005 | Huang | |
| 2005/0191375 A1 | 9/2005 | Babish et al. | |
| 2007/0077308 A1 | 4/2007 | Giner | |
| 2008/0089958 A1 | 4/2008 | Diehl et al. | |
| 2009/0028895 A1 | 1/2009 | Smith | |
| 2009/0104174 A1 | 4/2009 | Smith | |
| 2011/0223264 A1 | 9/2011 | Bouez et al. | |
| 2015/0056310 A1 | 2/2015 | Cenizo et al. | |

FOREIGN PATENT DOCUMENTS

| | | |
|---|---|---|
| CN | 1251302 A | 4/2000 |
| CN | 1367679 A | 9/2002 |
| CN | 1437929 A | 8/2003 |

(Continued)

OTHER PUBLICATIONS

Ryu et al, Cross-linking of collagen by singlet oxygen generated with UV-A. Chemical & pharmaceutical bulletin, (Aug. 1997) vol. 45, No. 8, pp. 1243-1247.*

(Continued)

*Primary Examiner* — Qiuwen Mi
(74) *Attorney, Agent, or Firm* — Drinker Biddle & Reath LLP

(57) ABSTRACT

The disclosed substance restores normal co-expression and interaction between the LOX and NRAGE proteins. Particularly, an effective amount of the substance that modulates the expression and/or activity of LOX of SEQ ID NO: 1 and/or that modulates the expression and/or activity of NRAGE of SEQ ID NO: 2, may be used for the manufacture of a composition for modulating the interaction between the LOX and NRAGE proteins to regulate the balance between the cellular phenomena of proliferation, differentiation and apoptosis, particularly in cases where the balance between these phenomena is disturbed, and especially in cases where the interaction between LOX and NRAGE is absent or altered. The invention makes it possible especially to treat and/or prevent skin ageing, lichen planus, graft-versus-host reaction (GVH), eczema, psoriasis and a cancer, particularly an epithelial cancer and more particularly a cutaneous epithelial cancer of basocellular or spinocellular type.

17 Claims, 8 Drawing Sheets

(56) References Cited

FOREIGN PATENT DOCUMENTS

| | | | |
|---|---|---|---|
| CN | 1484521 | A | 3/2004 |
| CN | 1589818 | A | 3/2005 |
| DE | 198 53 425 | A1 | 5/2000 |
| EP | 1 059 086 | A1 | 12/2000 |
| EP | 1498113 | A1 * | 1/2005 |
| EP | 1 570 851 | A1 | 9/2005 |
| EP | 2279736 | A1 | 2/2011 |
| FR | 2 723 096 | A1 | 2/1996 |
| FR | 2 777 192 | A1 | 10/1999 |
| FR | 2 779 348 | A1 | 12/1999 |
| FR | 2 837 702 | A1 | 10/2003 |
| FR | 2847267 | A1 | 5/2004 |
| FR | 2 849 992 | A1 | 7/2004 |
| FR | 2 855 969 | A1 | 12/2004 |
| JP | S58-192828 | | 11/1983 |
| JP | 61/263925 | A | 11/1986 |
| JP | H04-271759 | B2 | 9/1992 |
| JP | 2000/169383 | A | 6/2000 |
| JP | 2001/151634 | A | 6/2001 |
| JP | 2001/172157 | A | 6/2001 |
| JP | 2001/253830 | A | 9/2001 |
| JP | 2002/020225 | A | 1/2002 |
| JP | 2003/081850 | A | 3/2003 |
| JP | 2003081850 | A * | 3/2003 |
| JP | 2003/342190 | A | 12/2003 |
| JP | 2004/002237 | A | 1/2004 |
| JP | 2004/507582 | A | 3/2004 |
| JP | 2004/149729 | A | 5/2004 |
| JP | 2004/515523 | A | 5/2004 |
| JP | 2004/196765 | A | 7/2004 |
| WO | WO-94/23732 | A1 | 10/1994 |
| WO | WO-01/19850 | A2 | 3/2001 |
| WO | WO-01/20335 | A2 | 3/2001 |
| WO | WO-01/83702 | A2 | 11/2001 |
| WO | WO-02/17945 | A1 | 3/2002 |
| WO | WO-02/076487 | A1 | 10/2002 |
| WO | WO-03/084522 | A1 | 10/2003 |
| WO | WO-2004/045632 | A1 | 6/2004 |
| WO | WO-2004/064801 | A1 | 8/2004 |
| WO | WO-2005/092121 | A2 | 10/2005 |
| WO | WO-2006/029484 | A1 | 3/2006 |

OTHER PUBLICATIONS

Nam, N.-H., et al., "Antiinvasive, Antiangiogenic and Antitumour Activity of *Ephedra sinica* Extract", Phytotherapy Research, 2003, vol. 17, No. 1, pp. 70-76.

Sathiyamoorthy, P., et al., "Screening for Cytotoxic and Antimalarial Activities in Desert Plants of the Negev and Bedouin Market Plant Products", Pharmaceutical Biology, 1999, vol. 37, No. 3, pp. 188-195.

French Search Report issued in French application No. 0511112 dated Mar. 13, 2007.

International Search Report issued in PCT/FR2006/051117 dated Feb. 20, 2008.

Database WPI Week 200649, Derwent Publications Lt., London, GB; AN, 2006-472863, XP-002425451 & CN 1 723 951 A (Pharm Rest. Inst. Shandong Prov Medical Sci Acad), Jan. 25, 2006, Abstract.

Noblesse, E., et al.; "Lysyl Oxidase-Like and Lysyl Oxidase are Present in the Dermis and Epidermis of a Skin Equivalent and in Human Skin and Are Associated to Elastic Fibers", Journal of Investigative Dermatology, 2004, vol. 122, No. 3, pp. 621-630.

Smith-Mungo, L. I., et al.; "Lysyl Oxidase: Properties, Regulation and Multiple Functions in Biology", Matrix Biology, 1998, vol. 16, No. 7, pp. 387-398.

Pabuccuoglu, A., et al., "Antioxidant Activity of *Arbutus unedo* Leaves", Fitoterapia, 2003, vol. 74, pp. 597-599.

Revilla, E., et al., "Comparison of Several Procedures Used for the Extraction of Anthocyanins from Red Grapes", J. Agric. Food Chem., 1998, vol. 46, pp. 4592-4597.

Raskin, I., et al., "Can an Apple a Day Keep the Doctor Away?", Curr. Pharm. Des., 2004, vol. 10, No. 27, pp. 3419-3429.

Lee, J. Y., et al., "Loss of Elastic Fibers Causes Skin Wrinkles in Sun-Damaged Human Skin", Journal of Dermatological Science, 2008, vol. 50, No. 2, pp. 99-107.

Kavitha, O., et al., "Factors Influencing Collagen Biosynthesis", J. Cell Biochem., 2008, vol. 104, No. 4, pp. 1150-1160.

Ferrari, A., et al., "Evaluation of the Efficacy and Tolerance of a Topical Gel with 4% Quassia Extract in the Treatment of Rosacea", J. Clin. Pharmacol., 2012, vol. 52, No. 1, pp. 84-88.

Bonté, F., et al., "*Simarouba amara* Extract Increases Human Skin Keratinocyte Differentiation", J. Ethnopharmacol., 1996, vol. 53, No. 2, pp. 65-74.

Casetti, F., et al., "Dermocosmetics for Dry Skin: a New Role for Botanical Extracts", Skin Pharmacol. Physiol., 2011, vol. 24, No. 6, pp. 289-293.

Office Action issued in Japanese Application No. 2008-537164 Dated Nov. 17, 2015 with English Translation.

* cited by examiner

Figure 1: Sequence and diagram of the NRAGE protein (Neurotrophin-Receptor-interacting MAGE homolog or MAGE D1)

MAQKMDCGAGLLGFQAEASVEDSALLMQTLMEAIQISEAPPTNQATAAASPQSSQPPTANEM
ADIQVSAAAARPKSAFKVQNATTKGPNGVYDFSQAHNAKDVPNTQPKAAFKSQNATSKGPNA
AYDFSQAATTGELAANKSEMAFKAQNATTKVGPNATYNFSQSLNANDLANSRPKTPFKAWND
TTKAPTADTQTQNVNQAKMATSQADIETDPGISEPDGATAQTSADGSQAQNLESRTIIRGKR
TRKINNLNVEENSSGDQRRAPLAAGTWRSAPVPVTTQNPPGAPPNVLWQTPLAWQNPSGW
QNQTARQTPPARQSPPARQTPPAWQNPVAWQNPVIWPNPVIWQNPVIWPNPIVWPGPVVW
PNPLAWQNPPGWQTPPGWQTPPGWQGPPDWQGPPDWPLPPDWPLPPDWPLPTDWPLPP
DWIPADWPIPPDWQNLRPSPNLRPSPNSRASQNPGAAQPRDVALLQERANKLVKYLMLKDYT
KVPIKRSEMLRDIIREYTDVYPEIIERACFVLEKKFGIQLKEIDKEEHLYILISTPESLAGILGTTKD
TPKLGLLLVILGVIFMNGNRASEAVLWEALRKMGLRPGVRHPLLGDLRKLLTYEFVKQKYLDYR
RVPNSNPPEYEFLWGLRSYHETSKMKVLRFIAEVQKRDPRDWTAQFMEAADEALDALDAAAA
EAEARAEARTRMGIGDEAVSGPWSWDDIEFELLTWDEEGDFGDPWSRIPFTFWARYHQNAR
SRFPQTFAGPIIGPGGTASANFAANFGAIGFFWVE

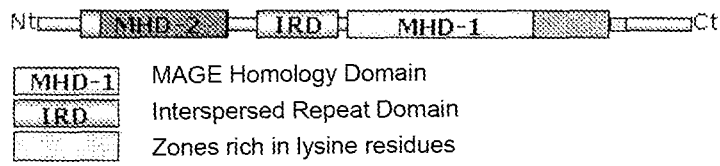

MHD-1   MAGE Homology Domain
IRD   Interspersed Repeat Domain
  Zones rich in lysine residues Figure 2: Mammalian two-hybrid interaction

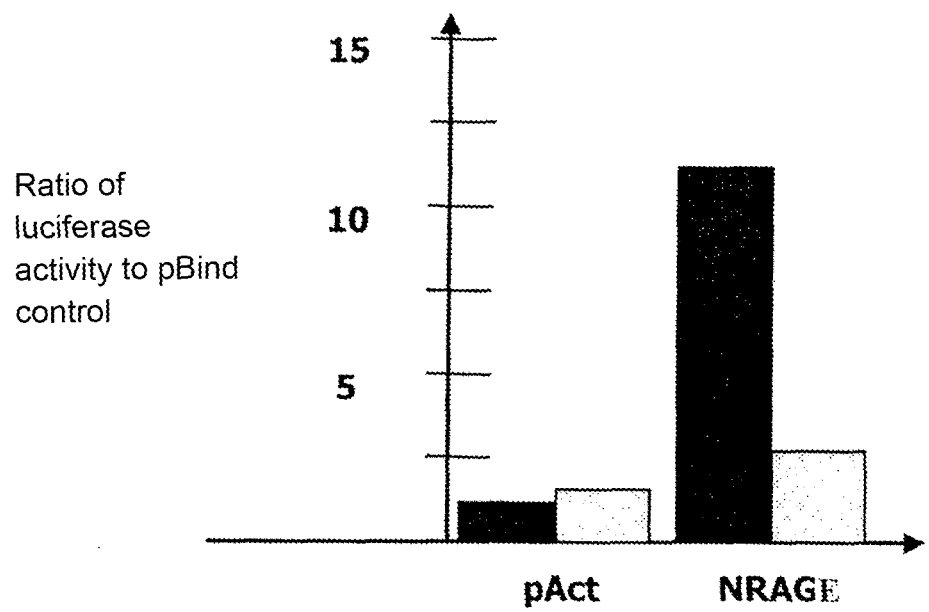

Figure 3: Identification of the presence of LOX and NRAGE in reconstructed skin (objective 25)
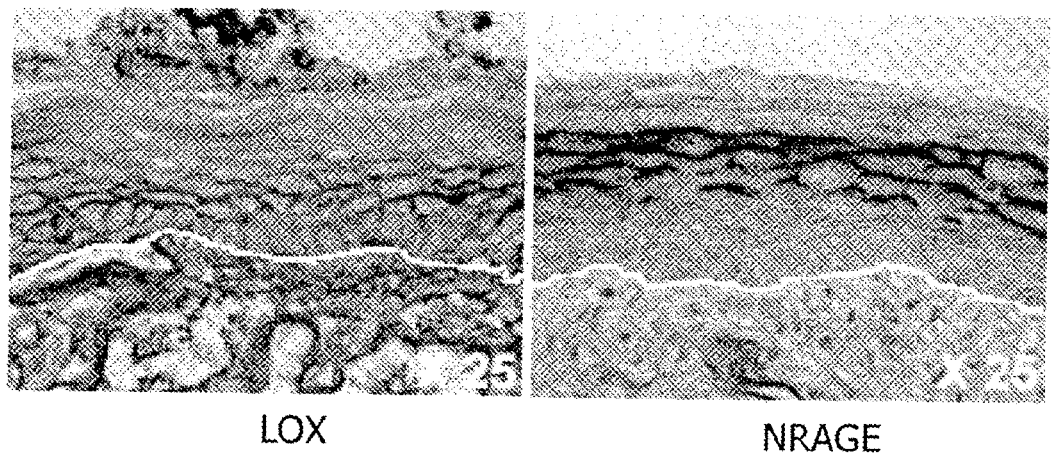
Figure 4: Co-location of LOX and NRAGE on human skin sections by confocal microscopy
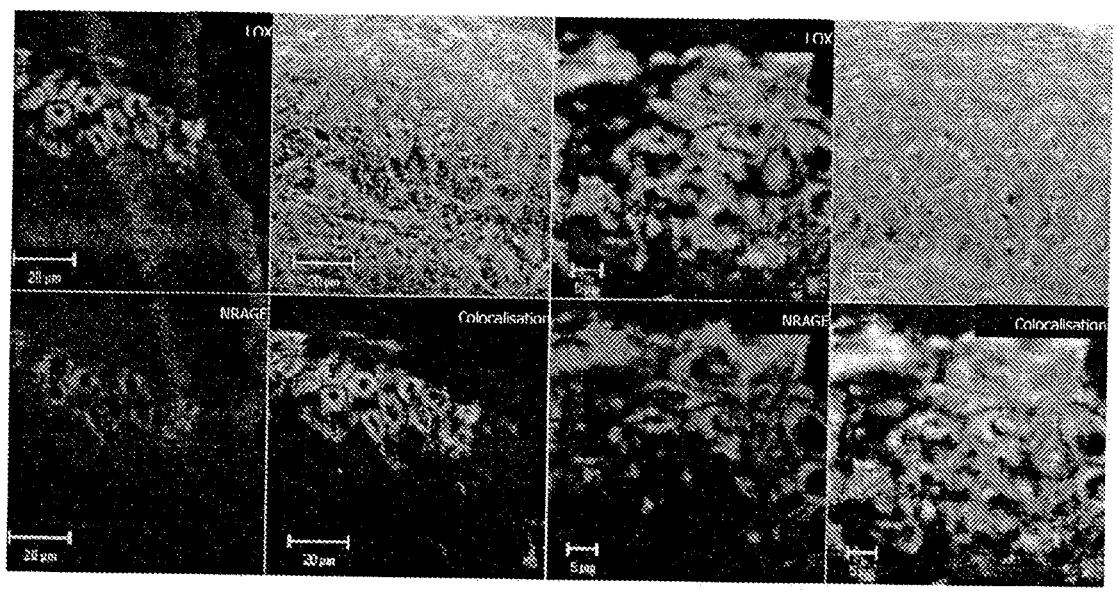

Figure 5: Immunodetection of LOX and NRAGE on human skin sections (91-year-old donor)
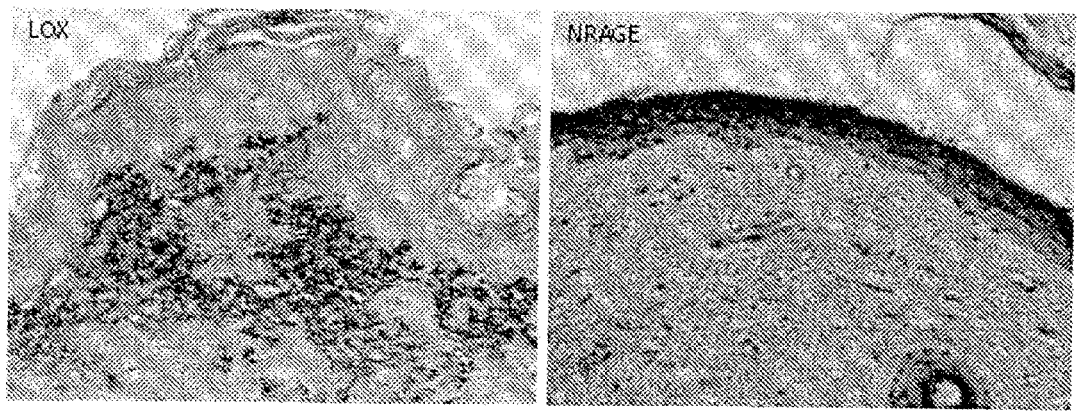
Figure 6: Detection of LOX and NRAGE in the skin of a person suffering from graft-versus-host reaction (GVH)
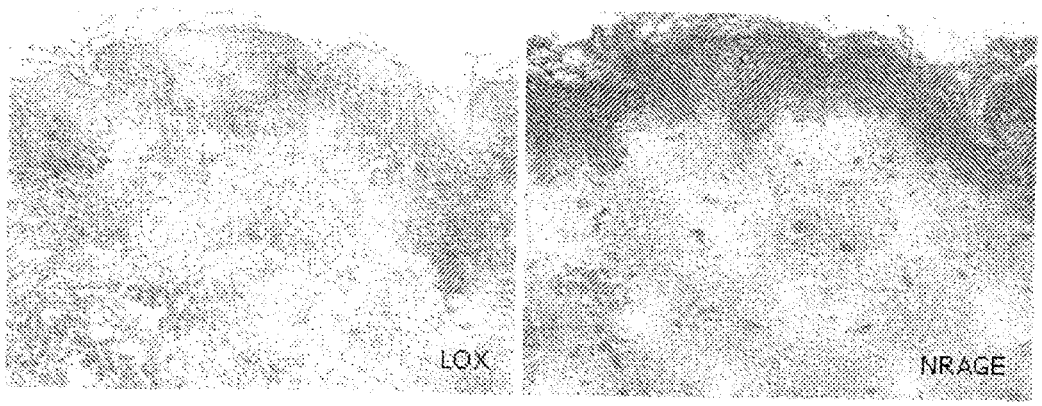

Figure 7: Detection of LOX and NRAGE in the skin of a person presenting with a cancer of basocellular and spinocellular type
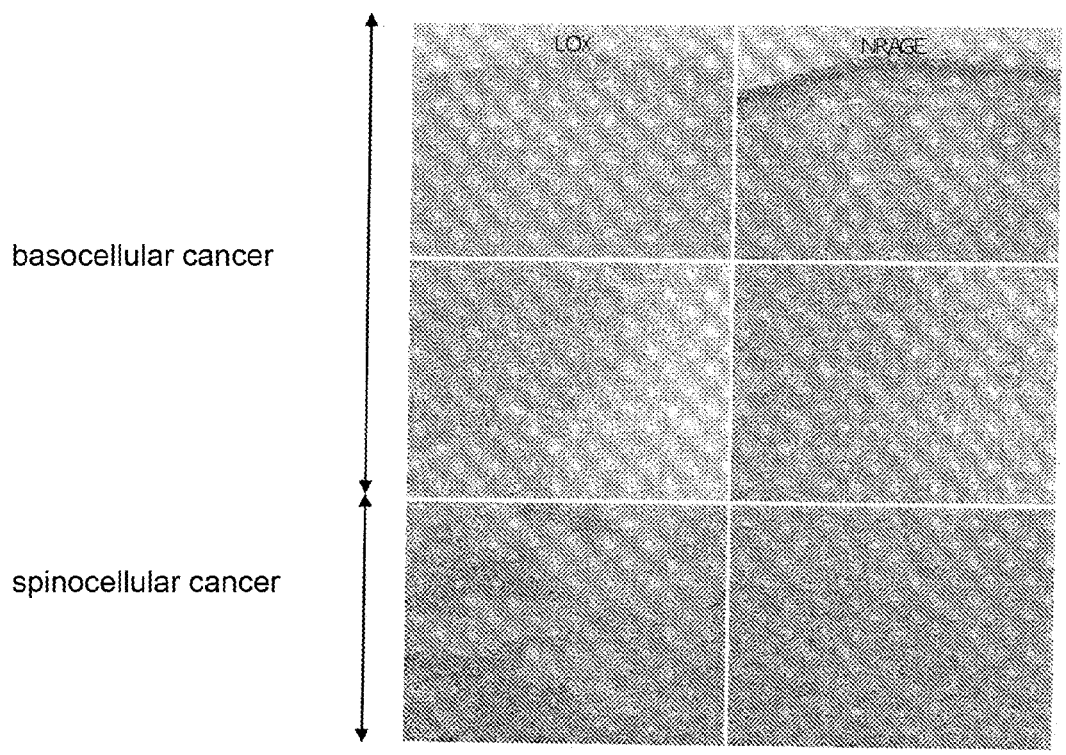
basocellular cancer
spinocellular cancer
Figure 8: Detection of LOX and NRAGE in the skin of a patient suffering from lichen planus
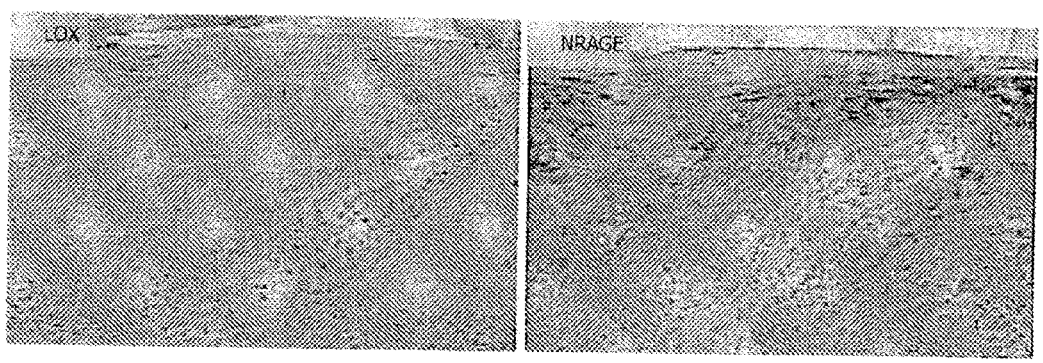

Figure 9: Identification of the location of LOX and NRAGE in the skin of a patient suffering from psoriasis
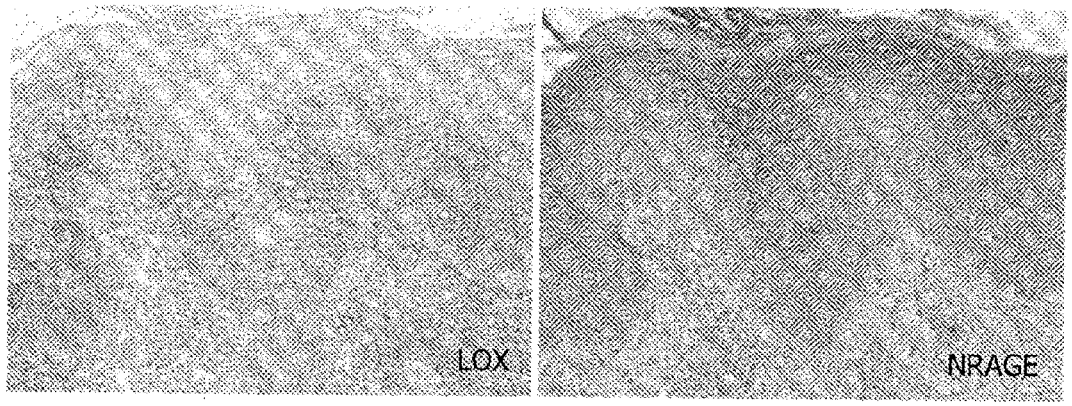
Figure 10: Identification of the location of LOX and NRAGE in the skin of a patient suffering from eczema
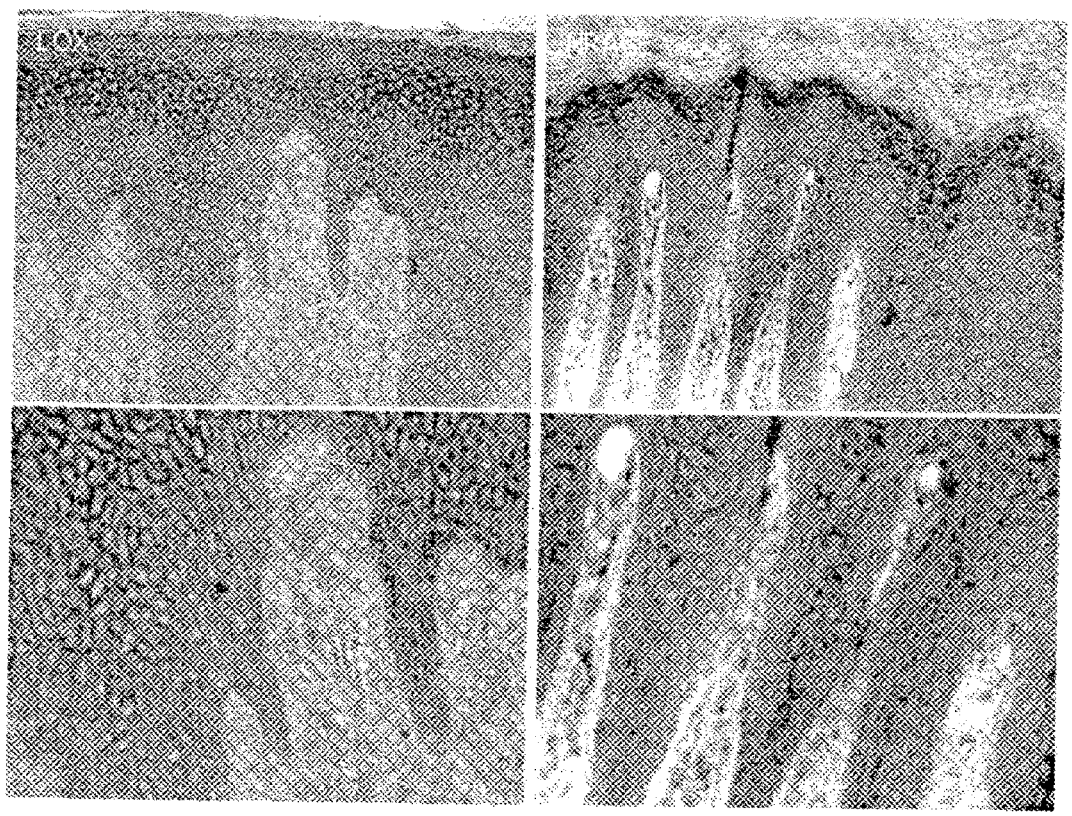

Figure 11
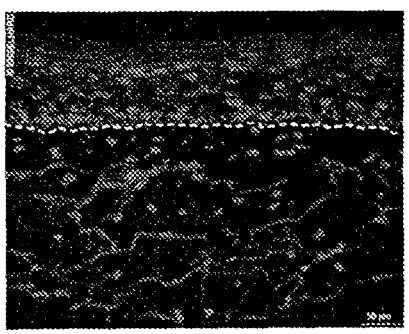
Not treated
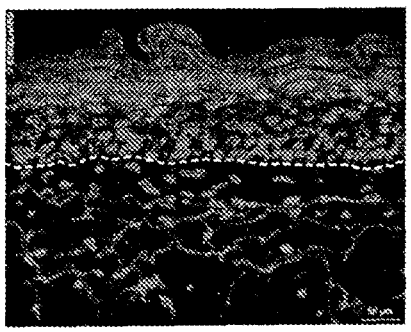
1.5 mM Ca
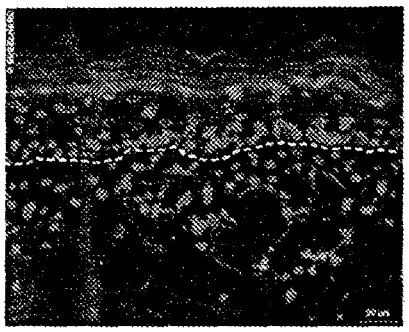
0.5% Ephedra
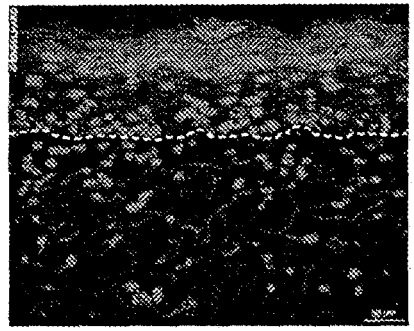
1% Ephedra
} Granular layers Figure 12
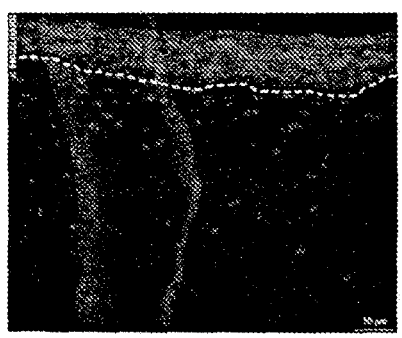
Not treated
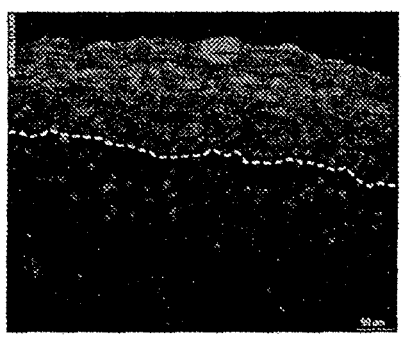
1.5 mM Ca
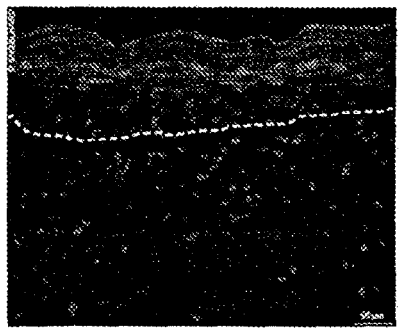
0.5% Ephedra
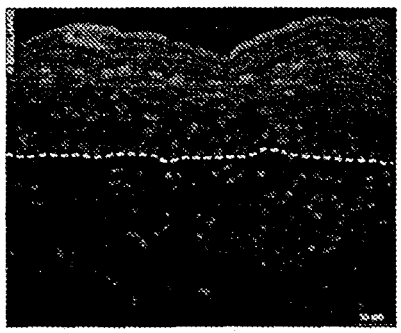
1% Ephedra
} Granular layers

SUBSTANCE FOR RESTORING NORMAL CO-EXPRESSION AND INTERACTION BETWEEN THE LOX AND NRAGE PROTEINS

RELATED APPLICATIONS

This application is a division of U.S. application Ser. No. 12/091,768, filed Nov. 26, 2008, which is incorporated by reference in its entirety and which is a national stage application under 35 U.S.C. §371 of PCT/FR2006/051117, filed Oct. 26, 2006, which claims priority of French patent application 0511112, filed Oct. 28, 2005, which is incorporated by reference in its entirety.

SUBMISSION OF SEQUENCE LISTING

The Sequence Listing associated with this application is filed in electronic format via EFS-Web and is hereby incorporated by reference into the specification in its entirety. The name of the text file containing the Sequence Listing is Replacement_Sequence_Listing_17587-00042 ST25.txt. The size of the text file is 16 KB, and the text file was created on Apr. 25, 2012.

STATE OF THE ART

1) Background

In multicellular organisms, homeostasis is maintained by a balance between cell proliferation, cell differentiation towards a defined function, and programmed or unprogrammed cell death.

The skin, for example, can be considered as an organ of which one specific function is to protect the organism from external aggressions. Impermeability to the outside is assured by a highly keratinized corneal layer composed of dead cells. The rhythm of the life of epidermal cells, or keratinocytes, is therefore governed by a succession of changes leading to this differentiation into keratinized and dead cells: (1) maintenance of initiator cells ("stem" cells of the basal cell layer of the epidermis), (2) asymmetric division (each stem cell giving two sister cells), (3) differentiation (formation of the suprabasal cell layers of the epidermis from one of the "initiator sister" cells), (4) acquisition of a resistance to apoptotic cell death, (5) change into cornified cells, and (6) programmed cell death of the upper cell layers of the epidermis. Any modification of this balance can be pathological.

Those skilled in the art are familiar with several biological mechanisms and molecules which take account of certain aspects of the cellular phenomena of proliferation, differentiation and apoptosis. However, no data give any real information about any one mechanism which would link these three phenomena and which would thus constitute a target on which to act with a view to controlling and regulating them.

2) LOX (Protein)

LOX belongs to the family of the lysyl oxidases (LOs), which are amine oxidases dependent on copper. 5 LO genes have been characterized to date: LOX LOXL, LOXL2, LOXL3 and LOXL4. Where LOX is known for its role in the crosslinking of collagen ex vivo and in vivo, LOXL is clearly associated with the homeostasis of elastic fibers. The in vivo role of the other isoforms is not known.

LOs are synthesized by a variety of cells such as fibroblasts, smooth muscle cells, endothelial cells and keratinocytes. This enzyme is therefore present in numerous tissues such as the skin, the liver, the kidneys, the spleen and the aorta, at both extracellular and intracellular levels.

2.1) Stabilization of the Extracellular Matrix—Extracellular Role

The extracellular role of LOX, which is now well known, consists in stabilizing the extracellular matrix (ECM) of connective tissues. The actual function of LOX is to crosslink fibrillar collagens and elastin. To do this, it catalyzes the oxidative deamination of lysyl and hydroxylysyl residues of fibrillar procollagen molecules and tropoelastin, this reaction being accompanied by the release of ammonia and hydrogen peroxide. The aldehyde residues formed then condense spontaneously with adjacent aldehyde or amine groups to form intramolecular and intermolecular bonds. These condensation reactions give rise to the bridging found in collagen and elastin fibers. LOX and LOs are therefore studied in biomedical fields that involve a change in the ECM (ageing, fibroses, cancer, healing, osteoarticular and cardiovascular diseases, angiogenesis).

It has been demonstrated in vitro that organic nitriles are irreversible LOX inhibitors. Thus β-aminopropionitrile (β-APN) binds to the active site of LOX in competition with alkylamine substrates; LOs use β-APN as substrate, thereby forming a Schiff base but without releasing the aldehyde product, which blocks the active site covalently without having an effect on synthesis. On this basis the inventors have described the use of different lysyl oxidase inhibitors, including β-APN, for avoiding the dedifferentiation of certain cell types (chondrocytes, etc.) which occurs systematically when these cells are cultivated (Farjanel et al., French patent 01.10443, CNRS, Use of lysyl oxidase inhibitors for cell culture and tissue engineering, filed on 3 Aug. 2001, publication no.: 2 828 206). However, said document relates to lysyl oxidases as a whole and not specifically to the LOX isoform; furthermore, it relates exclusively to inhibition of the dedifferentiation of cells cultivated in vitro, providing no teaching on the role of lysyl oxidases, or a fortiori of LOX, in maintenance of the balance between proliferation, differentiation and apoptosis, nor does it provide any teaching on novel partners or substrates for lysyl oxidases or LOX.

2.2) Intracellular Role

The intracellular role of LOX, and of LOs in general, is less well known. Thus, although it is acknowledged that LOX participates in the regulation of cell development, differentiation, mobility or senescence (Csiszar, Lysyl oxidases: A novel multifunctional amine oxidase family, Nucleic Acid Research and Molecular Biology, 2001, 70, 2-28), the underlying molecular mechanisms are not elucidated.

2.2.1) LOX and Cellular Homeostasis

The possible involvement of LOX in the regulation of cellular homeostasis (maintenance of a physiological balance between proliferation, differentiation and apoptosis) is commonly accepted (Jeay et al., Lysyl oxidase inhibits Ras-mediated transformation by preventing activation of NF-KB, Mol. Cell. Biol., 2003, 23, 2251-2263), but the underlying mechanisms are still unknown to those skilled in the art.

At the present time, those skilled in the art are thus in possession of a few data indicating a possible relationship between LOX and differentiation, on the one hand, and LOX and cell proliferation/transformation, on the other. However, the prior art does not refer to a possible relationship between LOX and apoptosis.

2.2.2) LOX and Epidermal Differentiation

LOX has been located in the epidermis, its expression being regulated as a function of the level of differentiation of keratinocytes (Noblesse et al., Lysyl oxidase-like and lysyl oxidase are present in the dermis and epidermis of a skin equivalent and in human skin and are associated to elastic fibers, J. Invest. Dermatol., 2004, 122, 621-630). However, the studies carried out hitherto have not made it possible to define the role of LOX in keratinocytes or to search for its partners in these cells, which make little or no collagen or elastin.

2.2.3) LOX and Cell Transformation

The LOX gene is clearly associated with maintenance of the non-tumoral phenotype of cells.

Two hypotheses have been put forward to explain this role of LOX. The first hypothesis suggests that crosslinking of the ECM induces a three-dimensional environment that favors maintenance of the non-tumoral state. This hypothesis is supported by the fact that LOX and LOXL are no longer expressed when cancers become invasive, whereas they are present in cancers in situ (Peyrol et al., Lysyl oxidase gene expression in the stromal reaction to in situ and invasive ductal breast carcinoma, Am. J. Pathol. February, 150(2), 497-507, 1997). The other hypothesis concerns the intracellular roles of LOs on substrates which those skilled in the art are yet to discover (Li et al., Localization and activity of lysyl oxidase within nuclei of fibrogenic cells, Proc. Natl. Acad. Sci. USA, 1997, Nov. 25, 94(24), 12817-22).

It has in fact been shown that the LOX enzyme is a suppresser of the ras oncogene and that somatic mutations in the gene are associated with various cancers (Contente et al., Expression of gene rrg is associated with reversion of NIH 3T3 transformed by LTR-c-H-ras, Science, 1990, 249, 796-798; Csiszar et al., Somatic mutations of the lysyl oxidase gene on chromosome 5q23.1 in colorectal tumors, Int. J. Cancer, 2002, 97, 636-642). Recent studies show that the low level of expression of LOX in fibroblasts transformed by ras is due to the activity of the FGF-2 autocrine growth factor and that the antitumoral drug suramine makes it possible to reinduce the expression of the enzyme (Palamakumbura et al., Autocrine growth factor regulation of lysyl oxidase expression in transformed fibroblasts, J. Biol. Chem., 2003, Aug. 15, 278(33), 30781-7; Epub 2003 Jun. 4). It has been shown elsewhere that the re-expression of LOX in these fibroblasts inhibits their growth in soft agar by acting on the NF-kB signaling pathway via regulation of the location of the AKT protein (Jeay et al., Lysyl oxidase inhibits Ras-mediated transformation by preventing activation of NF-B, Mol. Cell. Biol., 23, 2251-2263, 2003).

As in the case of other tumor suppressors, LOX probably acts according to the availability and regulation of its cellular substrates and partners, but the latter are still unknown to those skilled in the art.

2.2.4) Apoptosis

The term apoptosis is used to describe a particular form of cell death whose morphological characteristics differ from those of necrosis.

Apoptosis is a process of programmed cell death that requires the acquisition of caspases. In the course of this process the cells acquire particularly remarkable morphological characteristics, such as condensation of the chromatin and fragmentation of the nucleus, leading to their self-destruction and their elimination from the tissue without damaging the adjacent cells.

Apoptosis corresponds to the natural death of cells in the course of their development or during homeostasis.

The prior art provides information about a number of agents and mechanisms that are involved in regulating the cell cycle via the cellular processes of apoptosis and differentiation.

3) NRAGE (Protein)

Thus we are particularly familiar with one family of proteins that are involved in regulating the cell cycle, differentiation and apoptosis. It is the family of the MAGE (melanoma associated antigen) proteins, one of whose members, the NRAGE protein, which is also called "neurotrophin-receptor-interacting MAGE homolog", is particularly known for its proapoptotic role via the neurotrophic factor NGF.

The NRAGE protein comprises 778 amino acids. In the central region it carries a first domain characteristic of the MAGE proteins: the MAGE homology domain (MHD-1), and in the N-terminal region it carries a second domain: MHD-2, present only in certain isoforms. These two domains have zones rich in lysyl residues. Between these two domains there is a region called IRD (interspersed repeat domain), which does not exist in any other protein currently known.

The NRAGE protein is involved in controlling apoptosis via different pathways.

By interacting with p75NTR, which is the "low affinity" receptor of neutrophilic factors (NGF) or TNF, NRAGE can block the progression of the cell cycle and thus is proapoptotic via the caspase pathway.

NRAGE is also proapoptotic by interacting with cytoplasmic inhibitors of apoptotic proteins, IAP.

NRAGE can also act directly on the activity of nuclear homeo factors, such as the factors Msx and Dlx, which take part in the morphogenic regulation of tissues.

Although the expression of NRAGE is ubiquitous, the prior art does not refer to its presence in the skin, nor does it provide any data giving information about a possible relationship between LOX and apoptosis or about a link between LOX and NRAGE.

4) Conclusion on the Prior Art

The prior art does not provide the identity of novel partners or substrates for LOX, especially those taking part in maintenance of the cellular balance between proliferation, differentiation and apoptosis; moreover, the prior art does not provide the identity of these novel partners or substrates either in epithelial cells (particularly keratinocytes) or in any other cell type.

The prior art gives no information about the possible variations in the expression of LOX in the epidermis (especially LOX expressed by keratinocytes) as a function of age or of the existence or non-existence of exposure to UV or other types of aggression, or in the case of diseases affecting the skin (psoriasis, graft-versus-host reaction, cancers, etc.).

The prior art does not describe the involvement of LOX in apoptosis.

The prior art does not provide information about the possible presence of NRAGE in the skin, whether it be healthy skin, skin altered by age or UV or subjected to other types of aggression, or diseased skin.

The prior art does not offer known models for studying NRAGE in cells of epithelial origin or in the epidermis.

The prior art provides no information about any kind of interaction between LOX and NRAGE, irrespective of the tissue.

The prior art does not provide a model for identifying active principles capable of modulating the expression of LOX and/or NRAGE in keratinocytes.

Furthermore, animal experimentation is currently banned in Europe for certain applications and human experimentation is the subject of ethical debate. It is therefore unacceptable for the inventors to implement a screening method using animals or humans.

In the three-dimensional model MIMESKIN® (Coletica, France), LOX is expressed in the epidermis, its expression being regulated as a function of the level of differentiation of the keratinocytes (Noblesse et al., 2004). These studies did not include research into the expression of NRAGE or into the existence of a possible relationship between LOX and apoptosis, so it was not obvious that those skilled in the art would be interested in modulating the expression of LOX and/or NRAGE in order to regulate cellular homeostasis, based on the balance between proliferation, differentiation and apoptosis, in cases where it is disturbed (age, stress, disease), which thus constitutes a novel technical problem.

The prior art therefore fails to provide active principles capable of modulating the expression of intracellular partners for LOX (such as NRAGE), which may or may not be associated with modulation of the expression of LOX for the purpose of acting on cell regulation. In this context it is also very difficult to obtain objective criteria for judging the impact of these active principles.

BRIEF SUMMARY OF THE INVENTION

The invention relates to the use of a substance for restoring normal co-expression and interaction between the LOX and NRAGE proteins.

Objects of the Invention

The main object of the invention is to solve the technical problems referred to above, especially the technical problem relating to the provision of a method of identifying active principles for improving the interaction between the LOX and NRAGE proteins in cases where the interaction between LOX and NRAGE is absent or altered.

In particular the aim of the invention is to regulate the cellular balance between proliferation, differentiation and apoptosis in cases where it is disturbed, as in the case of skin altered by age or UV or subjected to other types of aggression, and/or in the case of pathological situations such as psoriasis, eczema, graft-versus-host reaction, lichen planus and/or cancerous diseases.

The invention further relates to the use of an active principle that modulates the expression of LOX and/or NRAGE for regulating the cellular balance between proliferation, differentiation and apoptosis, particularly in cases where it is disturbed, as in the case of skin altered by age or UV or subjected to other types of aggression, and/or in the case of pathological situations such as psoriasis, eczema, graft-versus-host reaction, and cancerous scars and/or diseases. In particular the invention relates to active principles for improving the interaction between the LOX and NRAGE proteins in cases where the interaction between LOX and NRAGE is absent or altered.

The invention makes it possible to solve the technical problem that consists in providing a method of locating the expression of NRAGE and following this expression, especially on a cellular model of skin. The invention makes it possible to solve the technical problem that consists in providing a method of diagnosing a state associated with poor regulation of the interaction between LOX and NRAGE.

DESCRIPTION OF THE INVENTION

The meanings of the terms used throughout the description, as understood by the inventors, are given below:

"LOX": the isoform of the human protein lysyl oxidase, LOX, as defined in particular by the amino acid sequence SEQ ID no. 1;

"NRAGE": the human protein NRAGE as defined in particular by the amino acid sequence SEQ ID no. 2;

"modulation of the expression of LOX": modulation of the gene coding for LOX, especially modulation of the expression of the messenger RNA coding for LOX, but also modulation of the synthesis of LOX from this messenger RNA, as well as modulation of the activity of LOX;

"modulation of the expression of NRAGE": modulation of the gene coding for NRAGE, especially modulation of the expression of the messenger RNA coding for NRAGE, but also modulation of the synthesis of NRAGE from this messenger RNA, as well as modulation of the biological effect of NRAGE.

These modulations must make it possible to reinduce a state of balance between proliferation, differentiation and apoptosis in situations where this balance is disturbed.

Active principles which are considered to be effective on LOX are preferably those affording a difference of about ±50% in the expression of the mRNA of LOX and/or a difference of about ±15% in the expression of LOX and/or the activity of LOX on a model, comprising at least one cell type exhibiting LOX expression and/or activity, in contact with these active principles, compared with the level of LOX expression and/or activity in a control model (generally without being brought into contact with the active principles).

Active principles which are considered to be effective on NRAGE are preferably those affording a difference of about ±50% in the expression of the mRNA of NRAGE and/or a difference of about ±15% in the expression of NRAGE and/or the biological effect of NRAGE on a model, comprising at least one cell type exhibiting NRAGE expression and/or activity, in contact with these active principles, compared with the level of NRAGE expression and/or activity in a control model (generally without being brought into contact with the active principles).

Thus, according to a first feature, the present invention relates to the use of an effective amount of at least one substance that modulates the expression and/or activity of at least the LOX protein of sequence ID no. 1, and/or that modulates the expression and/or activity of at least the NRAGE protein of sequence ID no. 2, for the manufacture of a composition for modulating the interaction between LOX and NRAGE in order to regulate the cellular balance between proliferation, differentiation and apoptosis, particularly in cases where the balance between these phenomena is disturbed, and especially in cases where the interaction between LOX and NRAGE is absent or altered.

The invention relates to the use of an effective amount of at least one substance that modulates the expression and/or activity of LOX of sequence ID no. 1, and/or that modulates the expression and/or activity of NRAGE of sequence ID no. 2, for the manufacture of a composition for improving the interaction between the LOX and NRAGE proteins in cases where the interaction between LOX and NRAGE is absent or altered.

The invention further relates to the use of an effective amount of at least one substance that modulates the expression and/or activity of at least the NRAGE protein of sequence ID no. 2, and that optionally modulates the expression and/or activity of the LOX protein of sequence ID no. 1, for the manufacture of a composition for preventing or treating at least one state in which the cellular balance between proliferation, differentiation and apoptosis is absent or altered.

Advantageously, the expression of LOX and/or NRAGE is modulated in epithelial cells, particularly in keratinocytes.

Advantageously, the purpose of said substance is to modulate the interaction between the LOX protein and the NRAGE protein, said interaction occurring especially in the IRD domain of the NRAGE protein.

Advantageously, the interaction between LOX and NRAGE comprises the polymerization of NRAGE, particularly its dimerization, by LOX-induced enzymatic catalysis.

Advantageously, the interaction between LOX and NRAGE involves the production of $H_2O_2$ resulting from the catalytic activity of LOX, the $H_2O_2$ then activating other molecules, for example neutral sphingomyelinase or NF-kB.

Advantageously, the interaction between LOX and NRAGE involves a non-enzymatic activity of LOX, particularly an activity exerted by the pro-region (A22-D169) of LOX.

Advantageously, the purpose of the substance is to treat and/or prevent a condition selected from the group consisting of exposure of cells to a stress, particularly exposure of cells to heat, or exposure of cells to radiation, particularly solar radiation, or exposure of cells to a toxic agent, for example a chemical or microbiological agent, skin ageing, lichen planus, graft-versus-host reaction (GVH), eczema, psoriasis and a cancer, particularly an epithelial cancer.

Advantageously, the purpose of the substance is to reduce cell proliferation in the case of hyperproliferation, particularly in a cancer, more particularly an epithelial cancer and most particularly a cutaneous epithelial cancer, of basocellular or spinocellular type, psoriasis or eczema.

Advantageously, the purpose of the substance is to reduce apoptosis in the epidermis in the case of substantial apoptosis, particularly during skin ageing, exposure of the skin to a stress, particularly exposure to heat, or exposure of the skin to radiation, particularly solar radiation, or exposure of the skin to a toxic agent, for example a chemical or microbiological agent, or graft-versus-host reaction (GVH).

Advantageously, the purpose of the substance is to increase cell proliferation in the case of cell hypoproliferation in the epidermis, particularly during ageing, exposure of the skin to heat, exposure of the skin to radiation, particularly solar radiation, or graft-versus-host reaction (GVH).

Advantageously, the purpose of the substance is to stimulate the expression of LOX, and optionally to inhibit the expression of NRAGE, during skin ageing, exposure of the skin to a stress, particularly exposure to heat, or exposure of the skin to radiation, particularly solar radiation, or exposure of the skin to a toxic agent, for example a chemical or microbiological agent, or graft-versus-host reaction (GVH).

Advantageously, the purpose of the substance is to stimulate the expression and/or activity of NRAGE, and optionally to inhibit the expression and/or activity of LOX, in the epidermis in order to prevent or treat psoriasis or eczema.

Advantageously, the purpose of the substance is to stimulate the expression of LOX and NRAGE in order to prevent or treat a cancer, particularly an epithelial cancer and more particularly a cutaneous epithelial cancer, of basocellular or spinocellular type, or lichen planus.

Advantageously, said composition is a cosmetic, neutraceutical, dermo-pharmaceutical or pharmaceutical composition.

Advantageously, the cellular balance between proliferation, differentiation and apoptosis is the balance between proliferation, differentiation and apoptosis of the keratinocytes.

Advantageously, the starting material used to prepare the active principles, in the case of plants (preferably roots, stems, barks, flowers, fruits, seeds, germs, gums, exudates, leaves or whole plants) or proteins, may or may not be sterilized by radiation, for example beta or gamma radiation preferably at a dose of 5 kGy, and is then reduced to powder if necessary, for example by grinding at room temperature. The powder is then e.g. dispersed at a rate of 2 to 5% (weight/weight) of powder, preferably 5%, either in a polar solvent, for example water, an alcohol, a glycol such as butylene glycol, or a polyol, and/or a mixture of polar solvents, advantageously a mixture of water with an alcohol, glycol or polyol (such as ethanol, glycerol, butylene glycol and other glycols, xylitol, etc.) in variable proportions, preferably a 75/25 or 50/50 water/butylene glycol mixture, or in an apolar solvent, for example an alkane, or a mixture of apolar solvents, or in a mixture of polar and apolar solvents. Preferably after stirring, e.g. magnetic stirring, for at least 2 hours, and optionally heating of the solvent, the sample is preferably clarified by decantation or centrifugation and then filtered, preferably on a 0.45 µm or 0.22 µm filter.

Advantageously, the starting material used to prepare the active principles, in the case of characterized molecules (e.g. molecules obtained by synthesis or hemisynthesis, biological molecules obtained by purification), is diluted in a solvent, preferably water or dimethyl sulfoxide (in a concentration preferably of between $10^{-6}$ M and $10^{-2}$ M and particularly preferably in the order of $10^{-4}$ M, or preferably of between 1% weight/weight and 5% weight/weight, depending on the molecules). The solution obtained is then optionally filtered, preferably on a 0.45 µm or 0.22 µm filter.

Advantageously, the active principles obtained by one of the methods described above are used in a final concentration preferably of between 0.01% volume/volume (v/v) and 10% (v/v) and particularly preferably of between 0.1% and 1% (v/v).

Advantageously, said substance is selected from the group consisting of a soya extract, an ephedra extract, a hop extract and a cinnamon extract.

According to a second feature, the invention relates to a method of identifying at least one active principle described above, the purpose of which is in particular to modulate the interaction between LOX and NRAGE in order to prevent or treat at least one state in which the cellular balance between proliferation, differentiation and apoptosis is absent or altered, characterized in that it comprises:

bringing the active principle into contact with at least one type of living cell capable of expressing the LOX protein (SEQ ID no. 1) and/or the NRAGE protein (SEQ ID no. 2), and analyzing the expression of LOX and/or NRAGE, especially to identify an active principle that modulates the expression and/or activity of LOX and/or NRAGE in order to improve the cellular balance between proliferation, differentiation and apoptosis.

The invention further relates to a method of identifying at least one active principle for modulating the interaction between LOX and NRAGE in order to improve the interaction between the LOX and NRAGE proteins in cases where the interaction between LOX and NRAGE is absent or altered, characterized in that it comprises:

bringing the active principle into contact with at least one type of living cell capable of expressing the LOX protein (SEQ ID no. 1) and/or the NRAGE protein (SEQ ID no. 2), and analyzing the expression of LOX and/or NRAGE, especially to identify an active principle that modulates the expression and/or activity of LOX and/or NRAGE in order to improve the interaction between the LOX and NRAGE proteins in cases where the interaction between LOX and NRAGE is absent or altered.

Advantageously, the balance between the proliferation, differentiation and apoptosis of said living cells capable of expressing the LOX and/or NRAGE protein, or the interaction between the LOX and NRAGE proteins, is absent or altered before they are brought into contact with the active principle.

Advantageously, the living cells are epithelial cells, particularly keratinocytes.

Advantageously, the method comprises analyzing the expression of the messenger RNAs of LOX and/or NRAGE.

Advantageously, the method comprises using quantitative RT-PCR with the following primers in particular:

for the LOX gene:

```
Sense
ACGTACGTGCAGAAGATGTCC

Antisense
GGCTGGGTAAGAAATCTGATG
``` for the NRAGE gene:

```
Sense
TGCACAGACATCAGCAGATGG

Antisense
TTCACGGATGATATCTCTCAGC
```

Advantageously, the method comprises analyzing the kinetics of expression of the messenger RNAs, for example by quantitative RT-PCR.

The invention further relates to a method for the cosmetic care or therapeutic treatment of a subject in whom the balance between the cellular phenomena of proliferation, differentiation and apoptosis in at least one cell type is disturbed, said method comprising improving the interaction between LOX and NRAGE by the application or administration of a substance that modulates the expression of LOX and/or NRAGE.

The invention further relates to a method for the cosmetic care or therapeutic treatment of a subject in whom the interaction between LOX and NRAGE is absent or altered, said method comprising the application or administration of a substance that modulates the expression and/or activity of LOX of sequence ID no. 1, and/or that modulates the expression and/or activity of NRAGE of sequence ID no. 2.

The invention further relates to a method for the cosmetic care or therapeutic treatment of a subject presenting with a state in which the cellular balance between proliferation, differentiation and apoptosis is absent or altered, said method comprising the application or administration of a substance that modulates the expression and/or activity of NRAGE, and optionally that modulates the expression and/or activity of LOX.

According to a third feature, the invention relates to a process for the preparation of a composition, comprising:

the use of a previously defined method of identification for identifying an active principle that modulates the expression and/or activity of LOX and/or NRAGE in order to improve the cellular balance between proliferation, differentiation and apoptosis, and the mixing of the active principle with at least one excipient in order to produce a cosmetic, neutraceutical, dermopharmaceutical or pharmaceutical composition for preventing or treating at least one state in which the cellular balance between proliferation, differentiation and apoptosis is absent or altered.

The invention further relates to a process for the preparation of a composition, comprising:

the use of a previously defined method of identification for identifying an active principle that modulates the expression and/or activity of LOX and/or NRAGE in order to improve the interaction between the LOX and NRAGE proteins, and the mixing of the active principle with at least one excipient in order to produce a cosmetic, neutraceutical, dermopharmaceutical or pharmaceutical composition for improving the interaction between the LOX and NRAGE proteins in cases where the interaction between LOX and NRAGE is absent or altered.

According to a fourth feature, the invention relates to a method of locating NRAGE, comprising the use of at least one anti-NRAGE antibody for detecting and locating the presence of NRAGE, particularly in a model of reconstructed skin comprising at least keratinocytes, or a section of skin, preferably a section of skin originating from a person whose epidermis exhibits a state in which the cellular balance between proliferation, differentiation and apoptosis is absent or altered.

According to a fifth feature, the invention relates to the use of an anti-NRAGE antibody for the preparation of a composition for detecting a modulation of the expression of NRAGE at the cellular level, particularly in epithelial cells and preferably in keratinocytes.

Advantageously, the purpose of the composition is to detect a state in which the cellular balance between proliferation, differentiation and apoptosis, or the interaction between LOX and NRAGE, particularly in the epidermis, is absent or altered, said state being selected from the group consisting of exposure of cells to a stress, particularly exposure of cells to heat, or exposure of cells to radiation, particularly solar radiation, or exposure of cells to a toxic agent, for example a chemical or microbiological agent, skin ageing, lichen planus, graft-versus-host reaction (GVH), eczema, psoriasis and a cancer, particularly an epithelial cancer and more particularly a cutaneous epithelial cancer, of basocellular or spinocellular type.

Advantageously, the composition also comprises an anti-LOX antibody for detecting a modulation of the expression of LOX at the cellular level, particularly in epithelial cells and preferably in keratinocytes.

Advantageously, the composition also comprises an anti-LOX antibody for detecting a modulation of the expression of LOX in keratinocytes.

Advantageously, the keratinocytes are human keratinocytes.

DETAILED DESCRIPTION OF THE INVENTION

Unexpectedly, the inventors have discovered an interaction between LOX and the NRAGE protein. This discovery is fundamental and is the starting point of the present invention. It actually shows LOX to be the protein which, being present at the intersection of the proliferation, differentiation and apoptosis pathways, is capable of controlling cellular homeostasis.

The inventors have also discovered that the NRAGE protein is present in particular in the epidermis and is expressed in particular by the keratinocytes. This discovery also enables the interaction between LOX and NRAGE to be made an action target for cosmetic care or treatments for restoring cellular homeostasis in situations where it is disturbed.

1) Discovery and Characterization of the LOX/NRAGE Interaction In Vitro

Having previously discovered the presence of LOX in the epidermis (Noblesse et al., Lysyl oxidase-like and lysyl oxidase are present in the details and epidermis of a skin equivalent and in human skin and are associated to elastic fibers, J. Invest. Dermatol., 122, 621-630, 2004), the inventors endeavored to determine the role(s) that LOX might play at this level, in the knowledge that its main currently acknowledged role—crosslinking of collagen and elastin—was rather unlikely in these cells, which make little or no collagen or elastin at the level where LOX was located.

With this objective in mind, they searched for protein partners for LOX by the yeast two-hybrid technique and a library of normal human skin keratinocyte cDNA was screened using the lure GAL4 BD-hLOXmat in particular, thereby making it possible to identify NRAGE as a potential partner for LOX (cf. Example 1).

Using the two-hybrid technique in Hela cells, the inventors then verified that this potential partnership was also observed in mammalian cells (cf. Example 2).

The next step consisted in determining whether the identification of this potential partnership between LOX and NRAGE could correspond to a direct physical interaction between these two proteins. This was carried out in particular by a technique involving co-immunoprecipitation of the LOX and NRAGE proteins produced after transfection of their genes into Cos 7 cells. The results obtained on the one hand confirmed the physical interaction between LOX and NRAGE and on the other hand made it possible to specify that LOX interacted with a particular region of NRAGE called IRD (interspersed repeat domain), which is a region specific to NRAGE in the family of the MAGE proteins (cf. Example 3).

In this context it should be pointed out at this stage that the discovery of the interaction between LOX and NRAGE is of very particular interest when one considers, in combination, on the one hand that the NRAGE protein contains two domains rich in lysyl residues, which could be favorable sites for its dimerization under the catalytic action of LOX, and on the other hand that it is precisely in the form of a dimer that the functionality of NRAGE seems to manifest itself.

With this discovery of the existence of a direct physical interaction between LOX and NRAGE in vitro, located in the IRD region of NRAGE, the inventors asked themselves the question whether this interaction also took place in vivo. It is essential to recall at this stage that, in contrast to LOX, the presence of NRAGE in the skin had never previously been described.

2) Identification of the Presence of NRAGE in Normal Human Skin and Reconstructed Normal Human Skin The inventors identified the expression of NRAGE in both the dermis and the epidermis of the skin (cf. Examples 4 and 5).

Within the framework of the present invention the inventors used a method of locating the expression of NRAGE in the skin.

In the epidermis the inventors demonstrated, unexpectedly, that NRAGE was not expressed homogeneously—as would have been expected of a protein whose presence is generally described as ubiquitous—but in the form of an expression gradient.

Reminder of the Structure of the Epidermis:

The epidermis is a stratified epithelium resting on a basal membrane which anchors it to the dermis. Its thickness varies from 60 to 100 µm on average and it consists of 4 continuous layers, from the deepest to the surface, resulting from a progressive differentiation of the keratinocytes:

the basal cell layer (single row of cells)
the prickle cell layer (5 to 6 monocellular layers)
the granular layer (1 to 3 monocellular layers)
the horny layer (5 to 10 monocellular layers)

Thus NRAGE is absent in the basal cell layer and appears in the first layers of differentiated keratinocytes, the labeling increasing in the horny layers. The labeling of the first suprabasal cell layers of the epidermis corresponds to that observed for LOX, which appears from the basal cell layer upwards. On the other hand, the labeling of LOX decreases in the upper layers of the epidermis, where NRAGE is present, so a distinction is made between the following 3 zones:

1 lower zone of the epidermis, comprising the basal cell layer and the first proliferative suprabasal cell layers, where only LOX is expressed;

1 intermediate zone extending from the first non-proliferative suprabasal cell layers to the first monocellular horny layers, in which LOX and NRAGE are co-expressed;

and 1 upper zone of the epidermis, where only NRAGE is expressed.

Observations at the cellular level show that LOX and NRAGE appear at the periphery of the cell, particularly in the submembranous region, NRAGE also appearing in the cytoplasm (cf. Examples 4 and 5).

The inventors thus identified, for the first time, the presence of NRAGE in the skin, both in the dermis and the epidermis. They also showed that the epidermis comprises a part in which both the LOX and NRAGE proteins are expressed and share the same location at the cellular level, especially in the keratinocytes, said location being the submembranous peripheral zone (NRAGE also being present in the cytoplasm).

The inventors thus demonstrated fulfilment of the conditions for the direct interaction they had identified in vitro to be able to take place in the epidermis in the zone where both LOX and NRAGE are located.

3) Identification of Disturbances of the Expression of LOX and/or NRAGE in the Epidermis with Age and in Certain Pathological Situations The inventors also demonstrated, unexpectedly, that skin ageing and a number of pathological situations are accompanied by disturbances of the expression of LOX and/or NRAGE in the epidermis.

3.1) State of LOX and NRAGE in the Epidermis 3.1.1) Skin of Elderly Persons

The skin of elderly persons is characterized by a hypoproliferative epidermis that is very thin (reduced to a few cell layers) and hyperkeratinized.

The inventors identified the total absence of LOX (detectable by the techniques used) in aged skin. On the other hand, NRAGE is strongly expressed, is located in the cytoplasm and appears from the first suprabasal cell layer upwards, without an expression gradient.

Thus the present invention makes it possible to stimulate the expression (and/or activity) of LOX, with or without inhibiting the expression (and/or activity) of NRAGE, so as to reinduce a regulated differentiation zone and/or apoptosis zone, in particular by restoring a LOX and NRAGE co-expression zone. This also thickens the skin, especially the epidermis.

Thus the purpose of the present invention is especially to correct or prevent the effects of skin ageing.

3.1.2) Graft-Versus-Host Reaction (GVH)

GVH is a disease which can arise following allografts of hemopoietic stem cells. It is associated with the effect of the immune cells (lymphocytes) contained in the graft on the patient's normal organs (especially the skin, liver and digestive tract). In the skin it manifests itself in the form of a maculopapular, pruriginous and inflammatory eruption.

Patients suffering from this disease have very thin skin with a highly apoptotic epidermis.

The histological study carried out by the inventors identified the absence of LOX and a very pronounced presence of NRAGE, which is located in the cytoplasm and appears from the first suprabasal cell layers upwards.

Thus the present invention makes it possible to stimulate the expression (and/or activity) of LOX, with or without inhibiting the expression (and/or activity) of NRAGE, in order to reinduce a LOX and NRAGE co-expression zone, enabling them to interact and resulting in a reduction in the cutaneous manifestations of GVH, this being accompanied especially by a thickening of the skin, particularly the epidermis.

Thus the present invention enables patients suffering from GVH to reduce the cutaneous manifestations of this disease.

3.1.3) Lichen Planus

Lichen is a skin disease of unknown cause which is characterized by the presence of violet, flat, solid, dry and very pruriginous papules a few millimeters in diameter.

The inventors identified a very large decrease in the expression of LOX, or even its total absence, and a very irregular expression of NRAGE. These observations certainly reflect a non-existent or very weak level of interaction between the two proteins studied.

Thus the present invention makes it possible to stimulate the expression (and/or activity) of LOX, with or without modulating the expression (and/or activity) of NRAGE, in order to reinduce a LOX and NRAGE co-expression zone, enabling them to interact and making it possible to return to a normal epidermal state.

Thus the present invention enables patients suffering from lichen planus to treat, reduce or prevent this disease.

3.1.4) Psoriasis

Psoriasis is a chronic skin disease characterized by erythematosquamous lesions. The fundamental feature of the disease is an increase in the rate of multiplication of the keratinocytes, which is responsible for a more rapid renewal and a thickening of the epidermis.

Histologically one observes a hyperproliferation of the cells involved in the first steps of terminal differentiation, i.e. an incomplete terminal differentiation, which is associated with the absence or very weak presence of apoptosis.

The inventors detected a very strong expression of LOX and a moderate presence of NRAGE with a more or less homogeneous labeling of the zones in question, showing no expression gradient. These characteristics of an intensity of expression that varies from the norm are coupled with much more important anomalies affecting the location of the proteins in question. Thus, in psoriatic skin, LOX is essentially expressed in the lower part of the epidermis and NRAGE solely in its upper part, the expression of the proteins thus being shifted without there being the overlap zone normally observed in healthy skin. At the cellular level NRAGE is observed only in the cytoplasm and not in the submembranous peripheral zone.

These observations show that, in psoriasis, although the LOX and NRAGE proteins are both present in the epidermis, they cannot interact directly with one another because they are not physically present in the same place. This absence of interaction results in dysfunctions observed in the epidermis, thus reflecting the role of the interaction between LOX and NRAGE in maintaining epidermal homeostasis.

Thus inhibition of the expression (and/or activity) of LOX, and/or optionally stimulation, preferably partial stimulation, of the expression (and/or activity) of NRAGE, makes it possible in particular to obtain an overlap zone of LOX and NRAGE expression in order to reinduce a regulated proliferation zone that makes it possible to reduce hyperproliferation by promoting apoptosis in the keratinocytes.

Furthermore, stimulation of the expression (and/or activity) of NRAGE, and/or inhibition, preferably partial inhibition, of the expression (and/or activity) of LOX, makes it possible in particular to obtain an overlap zone of LOX and NRAGE expression in order to reinduce a regulated proliferation zone that makes it possible to reduce hyperproliferation by promoting apoptosis in the keratinocytes.

Thus the present invention makes it possible to prevent and/or treat psoriasis or reduce some of its effects.

3.1.5) Eczema

Eczema is a skin complaint characterized clinically by blotches, more or less extensive, localized swellings, and weeping vesicles that subsequently form scabs, accompanied by intense itching. In its chronic phase eczema is complicated by a modification of the skin with thickening. Apoptosis is reduced in the epidermis.

The inventors identified a very strong expression of LOX located at the periphery of the cells. On the other hand, NRAGE is weakly expressed and is observed only in the cytoplasm, which certainly reflects a non-existent or very weak level of interaction between the two proteins studied.

Thus stimulation of the expression (and/or activity) of NRAGE, and/or inhibition, preferably partial inhibition, of the expression (and/or activity) of LOX, makes it possible to increase apoptosis and thereby to reduce some of the effects of eczema.

Thus the present invention makes it possible to prevent and/or treat eczema and in particular to reduce some of its effects.

3.1.6) Epithelial Skin Cancers

A distinction is made between two major types of epithelial skin carcinoma:

basocellular carcinoma (90% of cases) is an essentially local, slowly developing tumor which virtually never metastasizes. It results from an uncontrolled proliferation of the keratinocytes of the basal cell layer;

spinocellular carcinoma (10% of cases) has a much more aggressive local development and can metastasize. It originates from an uncontrolled proliferation of the keratinocytes of the prickle cell layer.

The inventors identified the absence of LOX and NRAGE in the invasive cells of the two types of cancer studied (basocellular and spinocellular cancers), with a progressive loss of LOX and NRAGE in the epidermis in the vicinity of the tumors. The inventors also observed that LOX is strongly expressed in the stromal reaction around the tumors, whereas NRAGE is absent in this reaction.

It may be noted at this stage that the loss of expression of LOX, which had never previously been identified in the case of these two types of cancer, is unexpected and is perhaps specific to epithelial cancers, since LOX is generally considered to be present in cancers in situ.

The loss of expression of NRAGE is completely novel as well and has never been described in any cancer.

Thus stimulation of the expression (and/or activity) of NRAGE and the expression (and/or activity) of LOX makes it possible to restore homeostasis. It is possible to bring about a reversion of the tumoral phenotype, especially in epithelial skin cancers.

3.2) Conclusion on the Studies on Pathological Tissues

On the basis of these observations the inventors were able to demonstrate that the situations involving a deregulation of the balance between proliferation, differentiation and apoptosis, whether this be in the epidermis of elderly subjects or subjects suffering from different diseases affecting the epidermis in particular, were systematically characterized by defects in the expression of LOX and/or NRAGE, said defects being likely to change their interaction or render it impossible.

This finding led the inventors to search for a means of restoring the balance between proliferation, differentiation and apoptosis by utilizing the control exerted by LOX or NRAGE, preferably by utilizing the LOX-NRAGE couple.

Thus, on the basis of these unexpected discoveries, the inventors provided methods of identifying active principles that modulate the expression of LOX and/or NRAGE in order to restore the control exerted by these proteins via their interaction, for the purpose of identifying active principles for the preparation of compositions, especially cosmetic or pharmaceutical compositions.

In this way, in the case of epidermal hypoproliferation (aged skin, GVH), which is characterized by an extremely thin epidermis and the absence of expression of LOX, the expression of LOX is stimulated, with or without inhibiting the expression of NRAGE, in order to reinduce, via modulation of the co-expression of LOX and NRAGE, a regulated differentiation and apoptosis zone that leads to a thickening of the skin.

In the case of epidermal hyperproliferation (psoriasis, eczema), where NRAGE is underexpressed, the expression of NRAGE is stimulated, with or without (slightly) inhibiting that of LOX, in order to promote apoptosis by reinducing a regulated proliferation zone (LOX/NRAGE overlap) and making it possible to stop the hyperproliferation.

In the case of a high level of apoptosis in the epidermis (aged skin, exposure of the skin to a stress, particularly exposure to heat, or exposure of the skin to radiation, particularly solar radiation, or exposure of the skin to a toxic agent, for example a chemical or microbiological agent, or graft-versus-host reaction—GVH), where NRAGE is overexpressed, the expression of NRAGE is inhibited, with or without stimulating the expression of LOX.

4) Identification of the Involvement of LOX in Cellular Apoptosis

Unexpectedly, the inventors identified the existence of a hitherto unknown link between LOX and apoptosis. Thus the data obtained reflect the antiapoptotic role of LOX in the keratinocytes, said role involving regulation of the proapoptotic protein NRAGE in particular.

5) Search for Active Principles

Active principles were identified in particular by analyzing the expression of the messenger RNAs of LOX and NRAGE, especially on keratinocytes in culture and preferably on human keratinocytes. The active principles whose activity is to be tested are placed in contact with the keratinocytes in culture for a sufficient time and under appropriate conditions for the contact to be effective. The active principles are preferably tested in different concentrations so that any influence of concentration can be detected.

Advantageously, the active principles screened in the present invention are of vegetable origin, in particular so as to avoid the problems associated with chemical synthesis. The advantages of active principles of vegetable origin are well known to those skilled in the art, especially in pharmacy, dermopharmacy, neutraceutics and cosmetics.

The search for active principles is carried out especially by extracting the total RNAs and then performing quantitative RT-PCR. In particular, the preferred primer sequences are those used in Example 13, without implying a limitation.

The amount of cDNA in each assay is plotted against the amount of actin cDNA. The effect of the presence or absence of active principles is then compared. If the expression and/or activity of NRAGE and/or LOX are modulated (stimulated or inhibited) relative to the controls, the substance can then be qualified as an active principle. Advantageously, an active principle makes it possible to modulate the expression of the messenger RNA of LOX and/or NRAGE by at least 50% or the expression and/or activity of LOX and/or NRAGE by at least 15%.

The compounds according to the present invention are prepared in the form of compositions, especially cosmetic, dermopharmaceutical or pharmaceutical compositions. The excipient for these compositions therefore contains e.g. at least one compound selected from the group consisting of preservatives, emollients, emulsifiers, surfactants, moisturizers, thickeners, conditioners, matting agents, stabilizers, antioxidants, texturizing agents, brightening agents, film-forming agents, solubilizers, pigments, colorants, perfumes and sun filters. These excipients are preferably selected from the group consisting of amino acids and their derivatives, polyglycerols, esters, cellulose polymers and derivatives, lanolin derivatives, phospholipids, lactoferrins, lactoperoxidases, sucrose-based stabilizers, vitamin E and its derivatives, natural and synthetic waxes, vegetable oils, triglycerides, unsaponifiables, phytosterols, plant esters, silicones and their derivatives, protein hydrolyzates, jojoba oil and its derivatives, liposoluble/water-soluble esters, betaines, amine oxides, plant extracts, sucrose esters, titanium dioxides, glycines and parabens, and particularly preferably from the group consisting of butylene glycol, steareth-2, steareth-21, glycol-15 stearyl ether, cetearyl alcohol, phenoxyethanol, methylparaben, ethylparaben, propylparaben, butylparaben, butylene glycol, natural tocopherols, glycerol, sodium dihydroxycetyl phosphate, isopropyl hydroxycetyl ether, glycol stearate, triisononanoin, octyl cocoate, polyacrylamide, isoparaffin, laureth-7, a carbomer, propylene glycol, glycerol, bisabolol, a dimethicone, sodium hydroxide, PEG-30 dipolyhydroxystearate, capric/caprylic triglycerides, cetearyl octanoate, dibutyl adipate, grapeseed oil, jojoba oil, magnesium sulfate, EDTA, a cyclomethicone, xanthan gum, citric acid, sodium laurylsulfate, mineral waxes and oils, isostearyl isostearate, propylene glycol dipelargonate, propylene glycol isostearate, PEG-8 beeswax, hydrogenated palm kernel glycerides, hydrogenated palm glycerides, lanolin oil, sesame oil, cetyl lactate, lanolin alcohol, castor oil, titanium dioxide, lactose, sucrose, low density polyethylene and an isotonic saline solution.

Advantageously, the abovementioned compositions are formulated in a form selected from the group consisting of an aqueous or oily solution, a cream or an aqueous or oily gel, particularly in a pot or tube, especially a shower gel or a shampoo; a milk; an emulsion, microemulsion or nanoemulsion, particularly an oil-in-water, water-in-oil, multiple or silicone emulsion; a lotion, particularly in a glass or plastic bottle, a dosing bottle or an aerosol; an ampoule; a syrup; a liquid soap; a hypoallergenic cleansing bar; an ointment; a foam; an injectable solution; an anhydrous, preferably liquid, pasty or solid product, for example in stick form, especially in the form of lipstick; a powder; and a tablet.

In the Figures:

FIG. 1 shows a sequence and a diagram of the NRAGE protein;

FIG. 2 shows the mean of the results obtained in Example 2 for the two-hybrid interaction;

FIG. 3 shows the identification of the presence of LOX and NRAGE in reconstructed skin;

FIG. 4 shows the location of LOX and NRAGE on human skin sections by confocal microscopy;

FIG. 5 shows the detection of LOX and NRAGE on human skin sections from a 91-year-old donor;

FIG. 6 shows the detection of LOX and NRAGE in the skin of a person suffering from graft-versus-host reaction;

FIG. 7 shows the detection of LOX and NRAGE in the skin of a patient presenting with a cancer of basocellular or spinocellular type;

FIG. 8 shows the detection of LOX and NRAGE in the skin of a patient suffering from lichen planus;

FIG. 9 shows the identification of the location of LOX and NRAGE in the skin of a patient suffering from psoriasis;

FIG. 10 shows the identification of the location of LOX and NRAGE in the skin of a patient suffering from eczema.

FIG. 11 shows the global labelling of the reconstructed skin with Evans blue (red epidermal layers, blue cells, red fibers of the dermal substrate, dermo-epidermal junction in dotted lines).

FIG. 12 shows the immuno-histochemical detection of cyto-keratin 10 on the reconstructed skin (cells strongly expressing the red label, the nuclei in blue, the dermo-epidermal junction in dotted lines).

Figure 13:
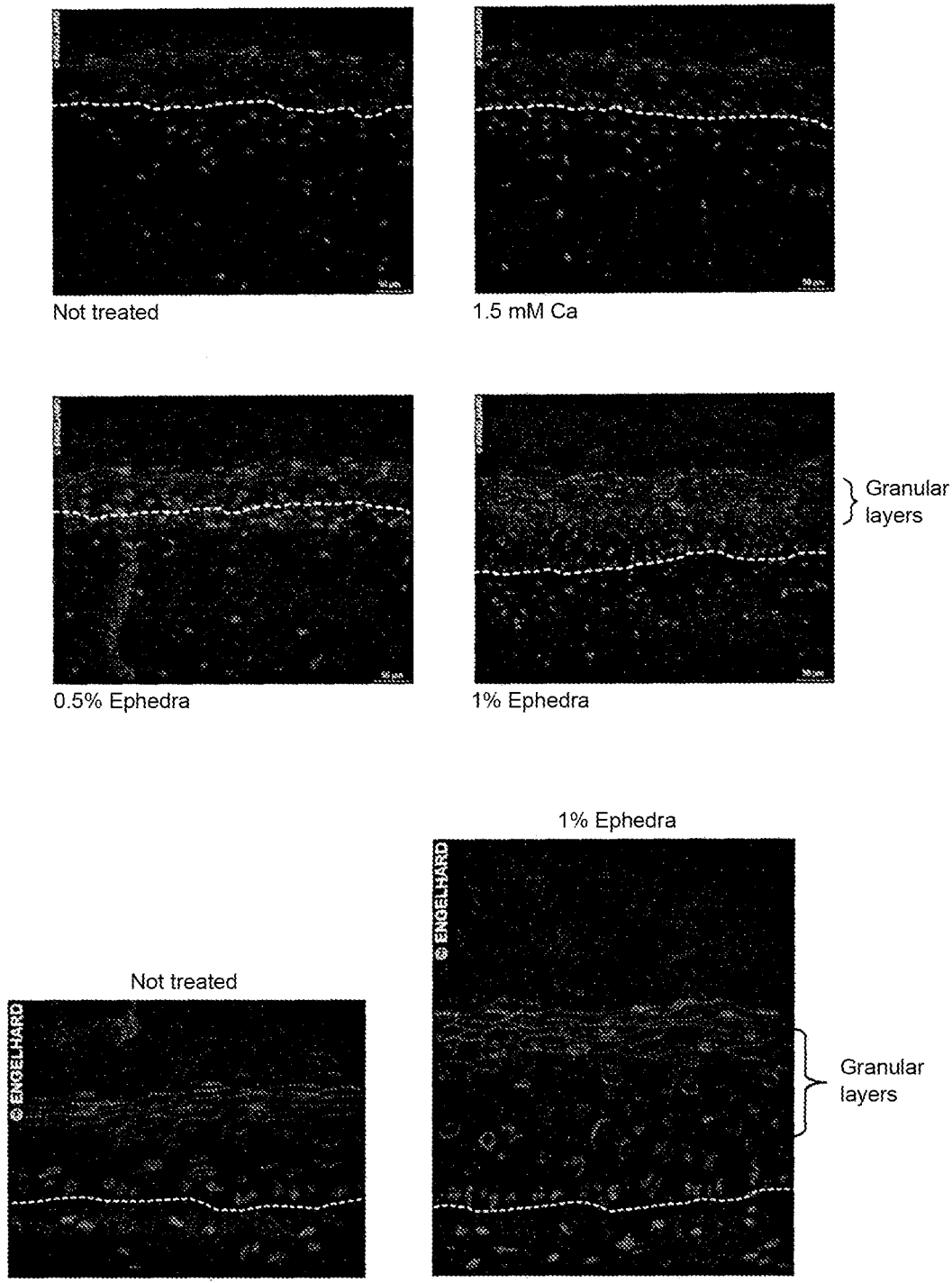
FIG. 13 shows the immuno-histochemical detection of transglutaminase on the reconstructed skin (cells strongly expressing the red label, the nuclei in blue, the dermo-epidermal junction in dotted lines).

Other objects, characteristics and advantages of the invention will become clearly apparent to those skilled in the art from the explanatory description referring to Examples, which are given solely by way of illustration and cannot in any way limit the scope of the invention.

The Examples form an integral part of the present invention and any characteristic that appears novel relative to any prior art on the basis of the description taken in its entirety, including the Examples, forms an integral part of the invention in its function and in its general applicability.

Each Example thus has a general scope.

Furthermore, in the Examples, unless stated otherwise, all the percentages are given by weight, the temperature is expressed in degrees Celsius and the pressure is atmospheric pressure.

EXAMPLES

Example 1

Cloning of NRAGE by the Yeast Two-Hybrid Technique

The invention initially consisted in searching for potential partners for LOX in keratinocytes. The yeast two-hybrid technique (Y2H) was employed. The Y2H system makes it possible to identify and characterize interactions between a "lure" protein and "target" potential partners. In the present case, the lure was the mature region of LOX fused to the DNA binding domain (BD) of the Gal4 gene. The target or targets were the genes encoded by a complementary DNA library of human keratinocytes, fused to the activation domain (AD) of the Gal4 gene. Interaction of the domains of the lure (LOX) with the domains encoded by a library sequence allows binding and activation of the Gal4 promoter, which controls different genes that confer auxotrophy to AH109 yeasts, enabling growth on deficient medium and activation of the galactosidase activities. A gene coding for a protein that was a candidate partner for LOX was thus identified by virtue of this technique for the possible selection of interactants: the intracellular protein Melanoma Associated Antigen D1 (MAGE-D1) or NRAGE (FIG. 1).

Screening of a Library of Keratinocytes by the Yeast Two-Hybrid Technique Using the Lure GAL4 BD-hLOXmat (Human LOX Mature)

The cDNA library of normal human skin keratinocytes in vector pGAD-10 was used. The lure chosen for this screening was LOXmat encoded by the human cDNA region of the LOX enzyme without the signal peptide or the pro-region. The nucleotide sequence was inserted in phase behind the DNA binding domain (BD) of the GAL4 transcription factor in vector pBD-Gal4 Cam. The LOX fragment +494 to +1254 to be inserted was amplified by PCR (polymerase chain reaction), and inserted behind the Gal4 binding domain in vector pGal4-BD, using the following primers:

```
1) ggg atc cgc atg gtg ggc gac gac
   (introducing Bam HI)

2) ttg tcg act aat acg gtg aaa ttg tgc
   (introducing Sal I at the stop which is
   conserved).
```

The amplified fragment was initially introduced into vector TOPO and then inserted into pGal4-BD. To validate the expression of the BD-LOXmat fusion protein, the AH109 yeasts were transformed by lure plasmid pBD-LOXmat.

The transformed yeasts are screened: $6.88 \times 10^6$ cfu (growth in deficient medium) in the AH109 yeast, 80 selected clones growing in adenine, histidine, tryptophan and leucine deficient medium, 23 of which were retained for their strong growth.

Example 2

Validation of the Interaction Between LOX and NRAGE by the Mammalian Two-Hybrid Technique (M2H)

Hela cells are transfected on the one hand by plasmids pAct and pAct-NRAGE and on the other hand by pBind and pBind-LOXmat in the presence of lipofectamine. The luciferase activity is tested after 48 h and the results are expressed as the ratio of luciferase activity to control (empty pBind vector). The experiments are performed in triplicate; the mean of the results obtained is shown in FIG. 2.

The hLOX sequence used in Example 1 for yeast two-hybrid screening was inserted in phase behind the Gal4 binding domain in the pBind vector (Promega, Madison, USA) for the mammalian two-hybrid interactions.

The NRAGE prey was inserted behind the VP16 Gal4 activation domain in the pAct vector (Promega). It starts at amino acid 152 (nucleotide 458).

Example 3

Co-Immunoprecipitation of LOX and NRAGE in Mammalian Cells

Cos 7 cells (mammalian kidney epithelial cells) are co-transfected for the LOX genes (human complete, human mature region and murine mature region) by the construct pcLOX32-V5His (LOX), pcLOX36-V5His or pcLOX27-V5His and for the NRAGE gene by pNM3-HA (complete NRAGE) or pNM7-HA (IRD region). The transfection is performed in Petri dishes 100 mm in diameter using lipofectamine. After 48 h the transfected cells are lyzed in 500 μl of lysis buffer. The proteins of the cell lyzates are incubated with either anti-V5 or anti-HA; the anti-V5 or anti-HA monoclonal antibody is added to the cell lyzate at a rate of 1/250 over 1 h 30 min at 4° C., with shaking.

The immune complexes (ICs) formed in this way are precipitated with protein G-Sepharose over 1 h at 4° C., with shaking. After three 10-minute washes in lysis buffer and elution in SDS-PAGE buffer, all the ICs are subjected to electrophoresis on a 10% SDS-PAGE gel, followed by Western blotting, Transfer of the ICs to a PVDF (polyvinylidene fluoride) membrane is followed by development:
  for NRAGE, with anti-HA diluted to 1/1000, then anti-mouse-HRP (horse radish peroxidase) diluted to 1/20,000,
  for LOX, with anti-V5-HRP diluted to 1/5000.

The final detection is effected by chemoluminescence of the HRP.

The results obtained demonstrate that the complete form of NRAGE (NM3-HA) co-immunoprecipitates with the human complete form of LOX (LOX 32H), mature human LOX (LOX 36H) and mature murine LOX (LOX 27H). Furthermore, NRAGE (NM7-HA), which corresponds to the IRD region, co-immunoprecipitates in the same way with these three recombinant proteins, showing the involvement of this region in the interaction.

Example 4

Identification, by Immunohistochemistry, of the Presence of LOX and NRAGE in a Model of Reconstructed Skin The identification was effected in a model of reconstructed skin (MIMESKIN®, Engelhard Lyon, France) prepared from a dermal substrate (collagen/glycosaminoglycans/chitosan, MIMEDISC®, Engelhard Lyon, France) inoculated with normal human fibroblasts, on whose surface normal human keratinocytes were deposited.

After 45 days of culture, allowing differentiation of the keratinocytes by exposure at the air-liquid interface, the samples are fixed in Bouin's fixative or formaldehyde and then included in paraffin.

Sections are immunolabeled with the antibodies described below:
  anti-LOX antibody obtained and purified by the method described by Sommer et al. (Transient expression of lysyl oxidase by liver myofibroblasts in murine schistosomiasis, Laboratory Investigation, 69, 460-470, 1993),
  anti-NRAGE antibody (goat polyclonal IgG),
  rabbit anti-goat secondary antibody.

The immune complexes are detected with a peroxidase-conjugated anti-rabbit IgG using diaminobenzidine as substrate, followed by counterstaining with hematoxylin.

FIG. 3 shows the immunohistochemical detection of LOX and NRAGE on the reconstructed skin.

The position of the dermo-epidermal junction is indicated by a continuous line, the position of the dermal substrate is indicated by an arrow and the location of the keratinocytes is indicated by an arrowhead.

The expression of LOX appears from the basal cell layer upwards, persists in the suprabasal cell layers and progressively disappears in the differentiated layers. The expression of NRAGE is slightly shifted; it asserts itself from the non-proliferative suprabasal cell layers upwards and intensifies greatly in the granular and horny layers, where LOX is no longer expressed.

These proteins are therefore associated in the non-proliferative suprabasal cell layers of the epidermis of the MIMESKIN® model of reconstructed skin. This co-location was confirmed by immunohistology (IH) on normal human skin.

The inventors thus demonstrated that the LOX and NRAGE proteins are expressed in the epidermis, with a co-location zone in the prickle cell layers.

Example 5

Identification of the Co-Location of LOX and NRAGE in Normal Human Skin by Confocal Microscopy Frozen sections of samples of normal human skin originating from surgical resection (foreskin) are prepared. The anti-LOX and anti-NRAGE primary antibodies of Example 4 were used to detect the expression of LOX and NRAGE. The secondary antibodies used are:
  donkey anti-rabbit IgG-F1TC, green fluorescein labeling,
  donkey anti-goat IgG-R, red rhodamine labeling.

A negative control was prepared in the absence of primary antibodies.

The dual labeling was observed using a ZEISS AXIOPLAN 2 LSM510 confocal upright microscope and the images were acquired using ZEISS LSM5 Image Browser software.

FIG. 4 shows the immunodetection of LOX and NRAGE in normal human skin by confocal microscopy.

The observations confirm the results of Example 4, further illustrating the co-location of LOX and NRAGE in the prickle cell layers of the epidermis of no mal human skin, with an almost perfect juxtaposition of the expression of LOX and NRAGE. Thus the observations at the cellular level show that LOX and NRAGE appear at the periphery of the cell (in the submembranous peripheral zone), NRAGE also appearing in the cytoplasm.

The inventors thus demonstrated fulfilment of the conditions for the direct interaction they had identified in vitro to be able to take place in the epidermis in the zone where both LOX and NRAGE are located.

Example 6

Identification of the Location of LOX and NRAGE in the Skin of Persons of Different Ages An immunohistological study using the protocol described in Example 4 was carried out on sections of human skin originating from 2 donors from different age groups (under 20 years and over 60 years).

FIG. 5 shows the labeling performed on the skin of a 91-year-old donor. The observations show a hypoproliferative epidermis that is very thin (reduced to a few cell layers) and hyperkeratinized.

The inventors identified the total absence of LOX (detectable by the technique used). On the other hand, NRAGE is strongly expressed, is located in the cytoplasm and appears from the first suprabasal cell layer upwards, without an expression gradient.

Example 7

Detection of LOX and NRAGE in the Skin of a Person Suffering from Graft-Versus-Host Reaction (GVH)

An immunohistological study using the protocol described in Example 4 was carried out on sections of human skin from patients suffering from graft-versus-host reaction (GVH). This study involved 5 different donors.

FIG. 6 identifies an almost total disappearance of LOX in the epidermis (without modification of its expression in the dermis) and a very pronounced presence of NRAGE, which is located in the cytoplasm and appears from the first suprabasal cell layers upwards.

Example 8

Detection of LOX and NRAGE in the Skin of a Person Presenting with a Cancer of Basocellular and Spinocellular Type An immunohistological study using the protocol described in Example 4 was carried out on samples of skin from patients presenting with a basocellular or spinocellular cancer.

FIG. 7 shows the following in both types of cancer studied:
a progressive decrease in the expression of LOX and NRAGE in the epidermis at the periphery of the tumors,
the absence of LOX and NRAGE in the epidermal invasive cells,
a strong expression of LOX in the dermal stromal reaction around the tumors,
the absence of NRAGE in the dermal stromal reaction around the tumors.

Example 9

Detection of LOX and NRAGE in the Skin of a Patient Suffering from Lichen Planus An immunohistological study using the protocol described in Example 4 was carried out on sections of skin from 3 patients suffering from lichen planus.

FIG. 8 shows a very large decrease in the expression of LOX in the epidermis, or even its total absence. This disturbance correlates with an irregularity in the expression of NRAGE in the epidermis.

Example 10

Identification of the Location of LOX and NRAGE in the Skin of a Patient Suffering from Psoriasis An immunohistological study using the protocol described in Example 4 was carried out on sections of skin from 5 patients suffering from psoriasis.

FIG. 9 is representative of all the sections observed and shows a very strong expression of LOX and a moderate presence of NRAGE in the epidermis, with a more or less homogeneous labeling of the zones in question, showing no expression gradient. These characteristics of an intensity of expression varying from the norm are coupled with much more important anomalies affecting the location of the proteins in question. Thus, in psoriatic skin, LOX is expressed essentially in the lower part of the epidermis and NRAGE solely in its upper part, the expression of the proteins thus being shifted without the overlap zone normally observed in healthy skin. At the cellular level, NRAGE is observed only in the cytoplasm and not in the submembranous peripheral zone.

Example 11

Identification of the Location of LOX and NRAGE in the Skin of a Patient Suffering from Eczema An immunohistological study using the protocol described in Example 4 was carried out on sections of skin from patients suffering from eczema.

FIG. 10 shows a very strong pericellular expression of LOX in the epidermis. On the other hand, NRAGE is weakly expressed and is observed only in the cytoplasm, which reflects a loss of co-location at the cellular level.

Example 12

Identification of the Involvement of LOX in the Inhibition of Apoptosis

The study was carried out on monolayer cultures of differentiated human keratinocytes at confluence. The effect of LOX on apoptosis was identified by inhibiting its activity through the addition of β-APN (0.02% w/v—(weight/volume)) under normal or proapoptotic conditions (thermal shock caused by exposure to a temperature of $45°$ C.$±0.5°$ C. for 1 h 30 min).

Cell death by apoptosis is detected and quantified using the TUNEL (terminal deoxynucleotidyl transferase mediated dUTP nick end labeling) technique, which is based on labeling of the DNA deletions accompanying apoptosis.

The first step consists in labeling the DNA breaks with TdT (terminal deoxynucleotidyl transferase), which catalyzes the polymerization of the fluorescein-labeled nucleotides at the free 3'-OH end of the DNA. The second step consists in detecting the incorporated fluorescein with an alkaline phosphatase-conjugated anti-fluorescein antibody after incubation with the substrate for the latter.

The experiment is validated by means of a positive control obtained by fragmentation of the DNA with a DNase solution, and a negative control obtained by depositing phosphate buffer.

The results obtained are shown in the Table below.

TABLE 1

|  | Without thermal shock (% of labeled cells) | With thermal shock (% of labeled cells) |
| --- | --- | --- |
| Without β-APN | 6% | 39% |
| With β-APN | 56% | 81% |

The results obtained demonstrate that:
thermal shock ($45°$ C.$±0.5°$ C. for 1 h 30 min) induces pronounced cellular apoptosis,
inhibition of the enzymatic activity of LOX by β-APN causes a substantial increase in apoptosis.

These results identify an antiapoptotic effect of the activity of LOX.

Example 13

Analysis of the Expression of LOX and NRAGE Messenger RNAs by Differentiated Keratinocytes in Culture in a Calcium Medium, with and without Contact with Active Principles Whose Activity is to be Tested (Analysis Performed e.g. by Quantitative RT-PCR, Screening of Active Principles)

The active principles were tested on keratinocytes of normal human foreskins from young subjects (pooled normal human foreskin epidermal keratinocytes—Clonetics).

The keratinocytes are amplified e.g. in K-SFM (keratinocyte serum-free medium), supplemented with antibiotics, up to the third passage at $37°$ C. under 5% $CO_2$.

The cells are inoculated into 96-well plates, e.g. at a rate of 40,000 cells per $cm^2$, and cultivated to about 80% confluence.

The cells are then cultivated in hypercalcium medium (1.7 mM $CaCl_2$ at 37° C. under 5% $CO_2$) to induce differentiation of the cells.

The starting material used to prepare the active principles, in the case of plants (preferably roots, stems, barks, flowers, fruits, seeds, germs, gums, exudates, leaves or whole plants) or proteins, may or may not be sterilized by radiation, for example beta or gamma radiation preferably at a dose of 5 kGy, and is then reduced to powder if necessary, for example by grinding at room temperature. The powder is then dispersed at a rate of 2 to 5% (weight/weight) of powder, preferably 5%, either in a polar solvent, e.g. water or butylene glycol, and/or a mixture of polar solvents, advantageously a mixture of water and an alcohol, glycol or polyol (such as ethanol, glycerol, butylene glycol and other glycols, xylitol, etc.) in variable proportions, and preferably a 75/25 or 50/50 water/butylene glycol mixture, or in an apolar solvent, e.g. an alkane, or a mixture of apolar solvents, or in a mixture of polar and apolar solvents. After stirring, e.g. magnetic stirring, for at least 2 hours, the sample is clarified by decantation or centrifugation and then filtered, preferably on a 0.45 μm or 0.22 μm filter.

The starting material used to prepare the active principles, in the case of characterized molecules (e.g. molecules obtained by synthesis or hemisynthesis, biological molecules obtained by purification), is diluted in a solvent, preferably water or dimethyl sulfoxide (in a concentration preferably of between $10^{-6}$ M and $10^{-2}$ M and particularly preferably in the order of $10^{-4}$ M, or preferably of between 1% weight/weight and 5% weight/weight, depending on the molecules). The solution obtained is then optionally filtered, preferably on a 0.45 μm or 0.22 μm filter.

The active principles obtained by one of the methods described above are then tested in a final concentration preferably of between 0.01% volume/volume (v/v) and 10% (v/v) and advantageously of between 0.1% and 1% (v/v), for example at 1% (v/v).

Incubation in the presence of the cells is advantageously carried out for 24 hours in hypercalcium K-SFM without growth factors. The cells are frozen dry at −80° C. after being rinsed in phosphate buffer pH 7.4.

Extraction of the Total RNAs

The total RNAs are extracted with the SV Total RNA Isolation System (Promega, Meylan, France) for the conditions of 96-well plates according to the manufacturer's protocol.

The gene expression is modified by real-time RT-PCR, measuring the expression of each gene relative to actin (housekeeping gene) and expressed in % of the untreated negative control.

Quantitative Real-Time RT-PCR (Q-RT-PCR)

10 μl of total RNAs at 5 ng/μl are added to 40 μl of PCR mix (composed of 25 μl of SYBR Green Buffer Mix 2×, 0.5 μl of enzyme mix, a final concentration of 0.5 μM of sense primer and a final concentration of 0.5 μM of antisense primer, and RNase and DNase free water qsp 40 μl).

The RT-PCR proceeds in different steps comprising retrotranscription at 50° C., 30 min, polymerase activation at 95° C., 15 min, and execution of the PCR cycles (95° C., 15 s; 60° C., 30 s; 72° C., 30 s)×50 cycles.

Production of the Fusion Curve

90° C., 1 min
30° C., 1 min
50° C. to 95° C., 10 s/° C. (fusion curve)

The percentage stimulation or inhibition is expressed relative to the untreated control (in the absence of test substance).

Actin Gene—Hybridization 60° C.

```
Sense
GTGGGGCGCCCCAGGCACCA

Antisense
CTCCTTAATGTCACGCACGATTTC
```

LOX Gene—Hybridization 60° C.

```
Sense
ACGTACGTGCAGAAGATGTCC

Antisense
GGCTGGGTAAGAAATCTGATG
```

NRAGE Gene—Hybridization 60° C.

```
Sense
TGCACAGACATCAGCAGATGG

Antisense
TTCACGGATGATATCTCTCAGC
```

Involucrin Gene—Hybridization 60° C.

```
Sense
TGTTCCTCCTCCAGTCAATACCC

Antisense
ATTCCTCATGCTGTTCCCAGTGC
```

To take account of the cell population present, all the results were compared with the "actin" signal used as a housekeeping gene. Depending on the experiment, the measurement threshold of the C(T) (=cycle threshold) was fixed for a value of T of between 0.05 and 0.01, an arbitrary unit of measurement then being calculated for each gene according to the following formula:

$$S\text{gene}<<x>> 10^7 \times (\tfrac{1}{2})^{C(T)\text{gene}<<x>>}$$

C(T)gene <<x>> denotes the number of cycles necessary to reach the fluorescence threshold of 0.01-0.05 of the gene <<x>>.

The values of the genes of interest were compared with the "actin" signal by calculation of the following ratio:

$$R = S\text{gene}<<x>> / S\text{actin}$$

These ratios were compared between the treated and untreated samples, <<x>> being the actin, LOX or NRAGE gene.

Screening of Active Principles

The amounts of cDNA in each assay are compared with the amount of actin cDNA and then with the negative controls (without active principles). The results are considered significant if the measured effect reaches a factor of about 2. Of 120 active principles tested, 3 correspond to these criteria at the concentrations tested and under the conditions defined. These active principles form the subject of the Table below:

TABLE 2

| Name | NRAGE Control multiplied by: | LOX Control multiplied by: |
| --- | --- | --- |
| Ephedra | 2 | 2 |
| Soya | 2.5 | 1 |
| Hops | 1 | 2 |

Preferably, the ephedra extract is obtained by extraction of the whole plant, especially with a polar solvent such as water or a water/butylene glycol mixture (e.g. 75/25 or 50/50), preferably water.

Preferably, the hop extract is obtained by extraction of the cones, especially with a polar solvent such as water or a water/butylene glycol mixture (75/25 or 50/50), preferably water.

Preferably, the soya extract is obtained by extraction of the seed, especially with a polar solvent such as water or a water/butylene glycol mixture (75/25 or 50/50), preferably water.

Conclusions

Of the bank of 120 active principles under the conditions considered:

1 active principle is capable of significantly activating the rate of synthesis of mRNA of the genes coding for NRAGE and LOX, 1 active principle is capable of significantly activating the rate of synthesis of mRNA of the gene coding for NRAGE, without having an effect on the gene coding for LOX, and 1 active principle is capable of significantly activating the rate of synthesis of mRNA of the gene coding for LOX, without having an effect on the gene coding for NRAGE.

This study made it possible to select active principles capable of modulating the balance between proliferation, differentiation and apoptosis, at least in the keratinocytes.

The ephedra extract can be used e.g. in the treatment of diseases such as cancers, preferably cutaneous epithelial cancers (basocellular or spinocellular), or lichen planus, or optionally in the treatment of certain cutaneous manifestations of GVH, or else to reduce the effects of ageing on the skin.

The soya extract can be used e.g. in the treatment of diseases such as cancers, like cutaneous epithelial cancers (basocellular or spinocellular), GVH or lichen planus, or for combating or preventing ageing. The soya extract can be used especially for combating cell hyperproliferation.

The hop extract can be used e.g. in the treatment of diseases such as cancers, like cutaneous epithelial cancers (basocellular or spinocellular), eczema or psoriasis. The hop extract can be used especially for combating cell hypo-proliferation.

The soya extract and hop extract can be used in association e.g. in the treatment of diseases such as cancers, like cutaneous epithelial cancers (basocellular or spinocellular), or lichen planus.

The soya extract and ephedra extract can be used in association e.g. in the treatment of diseases such as cancers, like cutaneous epithelial cancers (basocellular or spinocellular), or lichen planus.

The hop extract and ephedra extract can be used in association e.g. in the treatment of diseases such as cancers, like cutaneous epithelial cancers (basocellular or spinocellular), or lichen planus.

Example 14

Analysis, by Quantitative RT-PCR, of the Kinetics of Expression of the Messenger RNAs of NRAGE and LOX on Keratinocytes During Calcium Differentiation, and Effect of Active Principles on the Expression Kinetics The experimental conditions used to obtain cells at 80% confluence are identical to those described in Example 13. Differentiation takes place in the presence of calcium (1.7 mM $CaCl_2$) and active principle. An analysis is performed by Q-RT-PCR (method described in Example 13) after 2, 3 and 4 days of incubation.

Nine other substances were tested in this way. One of them, a cinnamon extract, affords an inhibition of LOX and NRAGE under the experimental conditions considered.

TABLE 3

| Name | NRAGE Control multiplied by | LOX Control multiplied by |
| --- | --- | --- |
| Cinnamon | | |
| 2 D | 0.9 | 0.5 |
| 3 D | 0.7 | 0.7 |
| 4 D | 0.2 | 0.5 |

(D = Days)

Preferably, the cinnamon extract is obtained by extraction of the bark, especially with a polar solvent such as water or a water/butylene glycol mixture (75/25 or 50/50), preferably water.

Conclusion

The cinnamon extract can be used e.g. in the treatment of diseases such as psoriasis.

The cinnamon extract and soya extract (whose effect was detected in the previous Example) can be used in association e.g. in the treatment of diseases such as certain cutaneous manifestations of GVH, eczema or psoriasis, or else for reducing the effects of ageing on the skin.

Example 15

Analysis of the Expression of LOX Messenger RNAs by Keratinocytes in Culture in the Absence of Calcium Differentiation, with and without their being Put into Contact with the Active Ingredients, the Activity of which is to be Tested (an Analysis for Example, Achieved by Quantitative RT-PCR, Screening of Active Ingredients)

The actives were tested on normal human keratinocytes from young subjects, obtained by enzymatic extraction of human biopsies collected after surgical resection and cultivated as monolayers in a K-SFM (keratinocyte serum free medium with supplements) defined medium, supplemented with antibiotics at 37° C. under 5% $CO_2$.

The cells are sown at the second passage in 24-well plates, for example with an amount of 30 000 cells per $cm^2$ and grown until about 95% confluence. The cell carpets are rinsed with phosphate buffer at pH 7.4 preferably with calcium and magnesium, before being put into contact with the active ingredients to be tested or the reference positive controls diluted in the K-SFM medium, prepared without supplements but with antibiotics.

Active ingredients of different origins (vegetable, biotechnological origin or synthesized molecules for example) are tested from 0.1% volume/volume (v/v) to 1% (v/v). An active ingredient from vegetable origin is tested for example at 1% (v/v) and a synthesized molecule is tested for example at 0.1% (v/v)

In particular, the active ingredient from vegetable origin are extracts which are obtained by macerating plants (preferably roots, rhizomes, stems, barks, flowers, fruit, seeds, germs or leaves) at 2-5% (w/w) in a solvent or a mixture of solvents, advantageously a 100:0 to 0:100 water/(alcohol, glycol or polyol) (such as ethanol, glycerol, butylene glycol and other glycols, xylitol, etc. . . . ) mixture. The obtained extracts are then filtered or distilled in order to recover the soluble fraction which is then filtered at 0.45 µm preferably. The biotechnological hydrolysates are obtained by fermentation of vegetable extracts in the presence of microorganisms, advantageously from the Lactobacillus or Saccharomyces family. These hydrolysates are then preferably filtered to 0.45 µm.

The incubation is advantageously performed for 24 hours at 37° C. under 5% $CO_2$, in a K-SFM medium without growth factors but with antibiotics. The negative controls are either the culture medium by itself, or the culture medium containing from 0.1% (v/v) to 1% (v/v) of the solvent used during the method for extracting the tested extracts. The reference positive control used for inducing cell differentiation is a solution of calcium chloride ($CaCl_2$—final concentration of 1.7 mM).

The untreated cells (NT control) are dry frozen at −80° C. after rinsing with pH 7.4 phosphate buffer. After treatment for 24 hrs in the presence of actives or controls, the cells are dry frozen at −80° C. after rinsing with pH 7.4 phosphate buffer.

Extraction of Total RNAs

The total RNAs are extracted by means of the SV total RNA isolation system (Promega, Meylan, France) for the conditions of 24-well plates according to the protocol of the manufacturer.

Modification of the expression of the genes is achieved by real time RT-PCR which measures the expression of each gene relative to actine (housekeeping gene) and expressed as a % of the untreated negative control (NT).

Quantitative Real Time RT-PCR (Q-RT-PCR)

10 µl of 5 ng/µl total RNAs are added to 40 µl of PCR mix (consisting of 25 µl of SYBR Green Buffer Mix 2×, 0.5 µl of enzyme mix, final 0.5 µM of sense primer and final 0.5 µM of antisense primer, RNAse-free and DNase-free water qsp 40 µl).

RT-PCR is performed in different steps including retrotranscription at 50° C., 30 min, activation of polymerase at 95° C., 15 min, performing PCR cycles, (95° C.-15 s, 60° C.-30 s, 72° C.-63 s, 78° C.-30 s)×50 cycles.

Producing the Melting Curve

90° C., 1 min
30° C., 1 min
50° C. to 95° C., 10 s/° C. (melting curve)

Primers Used:
Actine Gene—Hybridization at 60° C.

```
Sense
GTG GGG CGC CCC AGG CAC CA

Antisense
CTC CTT AAT GTC ACG CAC GAT TTC
```

LOX Gene—Hybridization at 60° C.

```
Sense
ACG TAC GTG CAG AAG ATG TCC

Antisense
GGC TGG GTA AGA AAT CTG ATG
```

In order to take into account the present cell population, all the results are relative to the "actine" signal, used as a housekeeping gene. According to the experimentation, the measuring threshold of C(T) (=cycle threshold) was set for T between 0.05 and 0.01 and then an arbitrary measuring unit is calculated for each gene according to the formula:

$$S\text{gene "LOX"} \; 10^7 \times (\tfrac{1}{2})C(T)\text{gene "LOX"}$$

C(T)gene "LOX" meaning the number of cycles required for reaching the fluorescence threshold of 0.01-0.05 of the "LOX" gene.

The values of the genes of interest were relative to the "actine" signal by calculating the ratio:

$$R = S\text{gene "LOX"}/S\text{actine.}$$

These ratios were compared between the treated and untreated samples.

Screening of Active Ingredients:

The cDNA amounts of each test are relative to the amount of cDNA of actine and then to the negative controls (NT). The results are considered as significative when the measured effect is a modulation by a factor of about 2 (stimulation) or 0.5 (inhibition). On 60 tested actives, 30 correspond to these criteria under the defined conditions. These actives are the following and are the subject of the Table herein below:

TABLE 1

| Description | Latin name | LOX modulation vs NT | Preferred part of the plant |
|---|---|---|---|
| Gypsophila | Gypsophila | 0.4 | Root |
| Red sandalwood | Pterocarpus santalinus | 0.4 | Total wood |
| Common bryony | Bryonia dioica | 0.5 | Root |
| Butcher's broom | Ruscus aculeatus | 2.0 | Root |
| Lemon | Citrus limonia | 2.0 | Fruit |
| Tangerine | Citrus reticulate | 2.1 | Fruit |
| Ethyl trans 3-hexanoate | | 2.3 | — |
| Khella | Amni Visnaga | 2.4 | Fruit |
| Alginic acid | | 2.4 | — |
| Carrot | Daucus Carota | 2.4 | Root |
| Methyl 2 methyl butyrate | / | 2.5 | — |
| Star anise | Illicium verum | 2.5 | Fruit |
| Cypress | Cupressus sempervirens | 2.6 | Fruit |
| Asae Foetida gum | | 2.6 | — |
| Xylitol | / | 2.8 | — |
| Hops | Humulus Lupulus | 2.8 | Fruit |
| Blackthorn | Prunus spinosa | 3.1 | Fruit |
| Strawberry tree | Arbutus unedo | 3.3 | Leaf |
| Umbellate wintergreen | Chimaphila umbellata | 3.4 | Plant |
| Sweet woodruff | Asperula odorata | 4.7 | Plant |
| Mugwort | Artemisia vulgaris | 4.7 | Root |
| Common elderberry | Sambucus nigra | 5.0 | Fruit |

TABLE 1-continued

| Description | Latin name | LOX modulation vs NT | Preferred part of the plant |
|---|---|---|---|
| Chinese cabbage | *Brassica Brassica campestris* var. *Pekinensis* | 5.3 | Plant |
| Cinnamon | *Cinnamomum* spp | 5.5 | Stem, bark |
| Chinese ephedra | *Ephedra sinica* | 6.0 | Plant |
| Bitter ash | *Cassia amara* | 6.2 | Total wood |
| Cacao tree | *Theobroma cacao* | 7.4 | Fruit shell |
| Silk | *Serica* | 7.9 | — |
| Red sarsaparilla | *Smilax ornate* | 9.0 | Root |
| Redcurrant | *Ribes rubrum* | 9.1 | Fruit |
| Pellitory | *Annacyclus pyrethrum* | 9.8 | Root |
| Sweet fennel | *Foeniculum* | 10.2 | Plant |

Conclusions

From the bank of 60 actives and under the considered conditions:

3 actives are capable of significantly inhibiting the synthesis rate of mRNA of the LOX coding gene,
  28 actives are capable of significantly activating the synthesis rate of mRNA of the LOX coding gene, With this study, it was possible to select active ingredients capable of modulating at least at keratinocyte level, the equilibrium between proliferation, differentiation and apoptosis.

Example 15

Analysis of the Expression of Proteins Involved in the Regulation of Epidermal Differentiation/Proliferation Homeostasis in a Reconstructed Skin Model with and without Contact with Active Ingredients, the Activity of which is to be Tested by Histology (Example of Ephedra Extract)

Demonstration of proliferation or differentiation labels was achieved in a reconstructed skin model (MIMESKIN®, Engelhard Lyons, France) prepared from a dermal substrate (collagen/glycosaminoglycans/chitosan, (MIMEDISK®, Engelhard Lyons, France) sown with normal human fibroblasts, at the surface of which normal human keratinocytes were deposited, the cells being extracted by enzyme treatment from biopsies obtained by surgical resection.

The reconstructed skin model is in particular achieved according to the following protocol:

0.5 to $1.10^6$ fibroblasts of normal human skin are sown on a matrix substrate based on collagen/glycosaminoglycan/chitosan, and then grown in a nutritive medium, for example DMEM-Glutamax supplemented with 10% of calf serum; ascorbic acid, preferably at a final concentration of 1 mM; EGF (epidermal grow factor), preferably at a final concentration of 10 ng/ml; Normocin, preferably at a final concentration of 100 µg/ml, for 21 days.
  0.5 to $1.10^6$ fibroblasts of normal human skin are sown on the dermal equivalent, and then grown in a nutritive medium, for example DMEM-Glutamax/Ham F-12 (ratio 3:1 v/v) supplemented with calf serum, ascorbic acid, preferably at a final concentration of 1 mM; EGF (epidermal growth factor), preferably at a final concentration of 10 ng/ml; hydrocortisone, preferably at a final concentration of 0.4 µg/ml; umuline, preferably at a final concentration of 0.12 IU/ml; isuprel, preferably at a final concentration of 0.4 µg/mg; triiodothyronine, preferably at a final concentration of $2.10^{-9}$M; adenine, preferably at a final concentration of 24.3 µg/ml; Normocin, preferably at a final concentration of 100 µg/ml. The culture was continued for 7 days in an immersed condition. The cultures were then placed at the air-liquid interface for 14 additional days in the same medium as the immersion culture, except for the calf serum, hydrocortisone, isuprel, triiodothyronine and umuline.

The active ingredient (ephedra extract) is advantageously diluted in the culture media described above at 0.5 and 1% and used 3 days after the respective sowing of fibroblasts and keratinocytes (i.e. days 3 to 21 and days 24 to 42). The positive control is preferably made by adding calcium chloride with a final concentration of 1.5 mM during the emerged phase of the reconstructed skins (i.e. day 28-42) in order to stimulate epidermal differentiation.

At the end of the culture, the samples are frozen, included into a thermosensitive resin, and then cryo-cut at 5 µm.

The labellings on the cuts were carried tout with the reagents described below:

human primary anti-transglutaminase antibody
  human primary anti-cytokeratin 10 antibody
  alexa-fluor coupled secondary antibodies
  Evans blue
  Dapi Viewing of immunolabellings is performed under photon microscopy (Axioskop2plus—Zeiss, Germany) and quantification of the transglutaminase immunolabellings was performed by image analysis (Lucia—Nilon, France) and the effects of the treatment with the active ingredient are evaluated (Holm-Sidak statistical test, $p<0.01$).

TABLE 1

Quantification of the labelling intensity of transglutaminase

| INTENSITY | Untreated | Calcium | Ephedra 0.5% | Ephedra 1% |
|---|---|---|---|---|
|  | 0.149 | 0.061 | 0.082 | 0.276 |
|  | 0.099 | 0.076 | 0.126 | 0.196 |
|  | 0.092 | 0.064 | 0.094 | 0.192 |
| Average | 0.113 | 0.067 | 0.100 | 0.221 |
| Standard deviation | 0.031 | 0.008 | 0.023 | 0.048 |
| Variation vs NT | 100% | 59% | 88% | 196% |
| Significance vs NT | — | No | No | Yes |
| Variation vs Ca | 169% | 100% | 149% | 330% |
| Significance vs Ca | No | — | No | Yes |

These results show that the active ingredient induces the same type of epidermal differentiation as the positive control with a dose-effect relationship. Indeed, the treated skins have a larger number of keratinocyte layers expressing transglutaminase, in particular in the so-called granular layer.

Moreover, the obtained labelling is more intense and more defined as illustrated in the magnification of the epidermal portion. Quantification clearly demonstrates induction of the protein form after treatment, in particular at 1% active ingredient concentration (2-fold induction).

FIG. 11 shows the global labelling of the reconstructed skin with Evans blue (red epidermal layers, blue cells, red fibers of the dermal substrate, dermo-epidermal junction in dotted lines).

These results show that the active ingredient induces the same type of epidermal differentiation as the positive control with a dose-effect relationship. Indeed, the treated skins have a larger number of differentiated keratinocyte layers and in particular, an increase in the thickness of the so-called granular layer is noted. Moreover, an interesting effect was also obtained on the fibroblast density at the dermas treated with ephedra extract.

FIG. 12 shows the immuno-histochemical detection of cyto-keratin 10 on the reconstructed skin (cells strongly expressing the red label, the nuclei in blue, the dermo-epidermal junction in dotted lines).

These results show that the active ingredient induces the same type of epidermal differentiation as the positive control with a dose-effect relationship. Indeed, the treated skins have a larger number of keratinocyte layers expressing cytokeratin 10 and in particular in the so-called granular layer.

FIG. 13 shows the immuno-histochemical detection of transglutaminase on the reconstructed skin (cells strongly expressing the red label, the nuclei in blue, the dermo-epidermal junction in dotted lines).

Example 17

Use of the Products of the Invention in Cosmetic or Pharmaceutical Formulations of the Oil-in-Water Emulsion Type Formulation 17a:

| | | |
|---|---|---|
| A | Water | qsp 100 |
| | Butylene Glycol | 2 |
| | Glycerol | 3 |
| | Sodium Dihydroxycetyl Phosphate, Isopropyl Hydroxycetyl Ether | 2 |
| B | Glycol Stearate SE | 14 |
| | Triisononanoin | 5 |
| | Octyl Cocoate | 6 |
| C | Butylene Glycol, Methylparaben, Ethylparaben, Propylparaben, pH adjusted to 5.5 | 2 |
| D | Products of the invention | 0.01-10% |

Formulation 17b:

| | | |
|---|---|---|
| A | Water | qsp 100 |
| | Butylene Glycol | 2 |
| | Glycerol | 3 |
| | Polyacrylamide, Isoparaffin, Laureth-7 | 2.8 |
| B | Butylene Glycol, Methylparaben, Ethylparaben, Propylparaben | 2 |
| | Phenoxyethanol, Methylparaben, Propylparaben, Butylparaben, Ethylparaben | 2 |
| | Butylene Glycol | 0.5 |
| D | Products of the invention | 0.01-10% |

Formulation 17c:

| | | |
|---|---|---|
| A | Carbomer | 0.50 |
| | Propylene Glycol | 3 |
| | Glycerol | 5 |
| | Water | qsp 100 |
| B | Octyl Cocoate | 5 |
| | Bisabolol | 0.30 |
| | Dimethicone | 0.30 |
| C | Sodium Hydroxide | 1.60 |
| D | Phenoxyethanol, Methylparaben, Propylparaben, Butylparaben, Ethylparaben | 0.50 |
| E | Perfume | 0.30 |
| F | Products of the invention | 0.01-10% |

Example 18 of the Invention

Use of the Products of the Invention in a Formulation of the Water-in-Oil Type

| | | |
|---|---|---|
| A | PEG-30 dipolyhydroxystearate | 3 |
| | Capric Triglycerides | 3 |
| | Cetearyl Octanoate | 4 |
| | Dibutyl Adipate | 3 |
| | Grapeseed Oil | 1.5 |
| | Jojoba Oil | 1.5 |
| | Phenoxyethanol, Methylparaben, Propylparaben, Butylparaben, Ethylparaben | 0.5 |
| B | Glycerol | 3 |
| | Butylene Glycol | 3 |
| | Magnesium Sulfate | 0.5 |
| | EDTA | 0.05 |
| | Water | qsp 100 |
| C | Cyclomethicone | 1 |
| | Dimethicone | 1 |
| D | Perfume | 0.3 |
| E | Products of the invention | 0.01-10% |

Example 19 of the Invention

Use of the Products of the Invention in a Formulation of the Shampoo or Shower Gel Type

| | | |
|---|---|---|
| A | Xanthan Gum | 0.8 |
| | Water | qsp 100 |
| B | Butylene Glycol, Methylparaben, Ethylparaben, Propylparaben | 0.5 |
| | Phenoxyethanol, Methylparaben, Propylparaben, Butylparaben, Ethylparaben | 0.5 |
| C | Citric acid | 0.8 |
| D | Sodium Laureth Sulfate | 40.0 |
| E | Product of the invention | 0.01-10% |

Example 20 of the Invention

Use of the Products of the Invention in a Formulation of the Lipstick Type and Other Anhydrous Products

| | | |
|---|---|---|
| A | Mineral Wax | 17.0 |
| | Isostearyl Isostearate | 31.5 |
| | Propylene Glycol Dipelargonate | 2.6 |
| | Propylene Glycol Isostearate | 1.7 |
| | PEG-8 Beeswax | 3.0 |

-continued

| | | |
|---|---|---|
| | Hydrogenated Palm Kernel Oil, Glycerides, Hydrogenated Palm Glycerides | 3.4 |
| | Lanolin Oil | 3.4 |
| | Sesame Oil | 1.7 |
| | Cetyl Lactate | 1.7 |
| | Mineral Oil, Lanolin Alcohol | 3.0 |
| B | Castor Oil | qsp 100 |
| | Titanium Dioxide | 3.9 |
| | CI 15850:1 | 0.616 |
| | CI 45410:1 | 0.256 |
| | CI 19140:1 | 0.048 |
| | CI 77491 | 2.048 |
| C | Products of the invention | 0.01-5% |

Example 20 of the Invention

Use of the Products of the Invention in an Aqueous Gel Formulation (Eye Contour Gel, Slimming Gel, etc.)

| | | |
|---|---|---|
| A | Water | qsp 100 |
| | Carbomer | 0.5 |
| | Butylene Glycol | 15 |
| | Phenoxyethanol, Methylparaben, Propylparaben, Butylparaben, Ethylparaben | 0.5 |
| B | Products of the invention | 0.01-10% |

Example 21 of the Invention

Use of the Products of the Invention in a Formulation of the Triple Emulsion Type

| | Primary emulsion W1/O | |
|---|---|---|
| A | PEG-30 dipolyhydroxystearate | 4 |
| | Capric Triglycerides | 7.5 |
| | Isohexadecane | 15 |
| | PPG-15 Stearyl Ether | 7.5 |
| B | Water | 65.3 |
| C | Phenoxyethanol, Methylparaben, Propylparaben, Butylparaben, Ethylparaben | 0.7 |
| | Secondary emulsion W1/O/W2 | |
| A | Primary emulsion | 60 |
| B | Poloxamer 407 | 2 |
| | Phenoxyethanol, Methylparaben, Propylparaben, 2-bromo-2-nitropropane-1,3-diol | 0.3 |
| | Water | qsp 100 |
| C | Carbomer | 15 |
| D | Triethanolamine | pH 6.0-6.5 |

Example 22 of the Invention

Preparation of Pharmaceutical Formulations Containing the Product of the Invention Formulation 22a: Preparation of Tablets

| | | |
|---|---|---|
| A | Excipients | In g per tablet |
| | Lactose | 0.359 |
| | Sucrose | 0.240 |
| B | Products of the invention* | 0.001-0.1 |

*The product of the invention is obtained e.g. by the extraction process described in Example 13, followed by a drying step.

Formulation 22b: Preparation of an Ointment

| | | |
|---|---|---|
| A | Excipients | |
| | Low density polyethylene | 5.5 |
| | Liquid paraffin | qsp 100 |
| B | Products of the invention* | 0.001-0.1 |

*The product of the invention is obtained e.g. by the extraction process described in Example 13, followed by a drying step, Formulation 22c: Preparation of an Injectable Formula

| | | |
|---|---|---|
| A | Excipient | |
| | Isotonic saline solution | 5 ml |
| B | Products of the invention* | 0.001-0.1 g |

*The product of the invention is obtained e.g. by the extraction process described in Example 13, followed by a drying step.

Example 23

Evaluation of the Cosmetic Acceptance of a Preparation Containing the Subject of the Invention The toxicology tests were performed on the compound obtained according to Example 2, incorporated at a concentration of 10% in a 0.5% xanthan gel, by carrying out an ocular evaluation in the rabbit, by studying the absence of abnormal toxicity by means of a single oral administration in the rat, and by studying the sensitizing power in the guinea-pig.

Evaluation of the Primary Cutaneous Irritation in the Rabbit:

The preparations described above are applied undiluted in a dose of 0.5 ml to the skin of 3 rabbits according to the method recommended by the OECD directive relating to the study of "the acute irritant/corrosive effect on the skin".

The products are classified according to the criteria defined by the decree of Feb. 1, 1982 published in the OJRF of Feb. 21, 1982.

The results of these tests afforded the conclusion that the products of the invention were classified as non-irritant on the skin.

Evaluation of the Ocular Irritation in the Rabbit:

The preparations described above were instilled pure in a single administration of 0.1 ml into the eye of 3 rabbits according to the method recommended by OECD directive no. 405 of 24 Feb. 1987 relating to the study of "the acute irritant/corrosive effect on the eyes".

The results of this test afford the conclusion that the preparations can be considered as non-irritant on the eyes, in terms of directive 91/326 EEC, when used pure or undiluted.

Test on the Absence of Abnormal Toxicity by a Single Oral Administration in the Rat:

The preparations described were given in a single oral administration in a dose of 5 g/kg body weight to 5 male rats and 5 female rats according to a protocol based on OECD directive no. 401 of 24 Feb. 1987 and adapted to cosmetic products.

The $LD_0$ and $LD_{50}$ are found to be above 5000 mg/kg. The preparations tested are not therefore classified as dangerous preparations on ingestion.

Evaluation of the Cutaneous Sensitizing Potential in the Guinea-Pig:

The preparations described are subjected to the maximization test described by Magnusson and Kligmann, the protocol being in accordance with OECD directive no. 406.

The preparations are classified as non-sensitizing on contact with the skin.

The invention claimed is:

1. A method for treating a skin condition by stimulating expression or activity, or for stimulating both expression and activity, of a LOX having the amino acid sequence of SEQ ID NO: 1, comprising topically administering an effective amount of a *Quassia amara* extract onto skin of a human having a skin condition selected from the group consisting of:
   (i) a skin condition where cellular balance between proliferation, differentiation and apoptosis is disturbed in the skin;
   (ii) exposure of skin to a stress;
   (iii) exposure of skin to radiation; and
   (iv) exposure of skin to a toxic agent,
   wherein the extract stimulates expression or activity, or both expression and activity, of the LOX in epithelial cells of the skin,
   and wherein the *Quassia amara* extract is a water extract wherein said water extract is obtained by macerating *Quassia amara* at 2-5% (w/w) in water.

2. The method of claim 1, wherein the extract further inhibits or stimulates expression of an NRAGE having the amino acid sequence of SEQ ID NO: 2.

3. The method of claim 2, wherein the extract stimulates the expression of the LOX.

4. The method of claim 1, wherein the extract stimulates the expression of the LOX.

5. The method of claim 4, wherein the *Quassia amara* extract is obtained from *Quassia amara* total wood.

6. The method of claim 1 for treating skin ageing.

7. The method of claim 1, wherein the extract is used in a cosmetic or nutraceutic composition at a final concentration of 0.01% volume/volume to 10% volume/volume.

8. The method of claim 7, wherein the extract is used in a final concentration from 0.1% volume/volume to 1% volume/volume.

9. The method of claim 1, wherein the extract is mixed with at least one excipient selected from the group consisting of preservatives, emollients, emulsifiers, surfactants, moisturizers, thickeners, conditioners, matting agents, stabilizers, antioxidants, texturizing agents, brightening agents, film-forming agents, solubilizers, pigments, colorants, perfumes and sun filters.

10. The method of claim 1, wherein the extract is identified by first bringing an active principle into contact with at least one type of living cell capable of expressing the LOX protein having the amino acid sequence of SEQ ID NO: 1, and then analyzing the expression of the LOX protein.

11. The method of claim 1, wherein the skin condition is exposure of skin to a stress, and wherein said stress is heat.

12. The method of claim 1, wherein the skin condition is exposure of skin to radiation, and wherein said radiation is solar radiation.

13. The method of claim 1, wherein the skin condition is exposure of skin to a toxic agent, and wherein said toxic agent is a chemical or microbiological agent.

14. The method of claim 1, wherein the epithelial cells are keratinocytes.

15. The method of claim 1, wherein the effective amount of the *Quassia amara* extract reduces apoptosis in epidermis in the case of substantial apoptosis during skin ageing.

16. The method of claim 1, wherein the effective amount of the *Quassia amara* extract increases cell proliferation in the case of cell hypoproliferation in epidermis during ageing or during exposure of skin to a stress, solar radiation, or a toxic agent.

17. The method of claim 1, wherein the LOX controls cellular homeostasis.

\* \* \* \* \*

SEQUENCE LISTING

<160> NUMBER OF SEQ ID NOS: 4

<210> SEQ ID NO 1
<211> LENGTH: 417
<212> TYPE: PRT
<213> ORGANISM: Homo sapiens

<400> SEQUENCE: 1

```
Met Arg Phe Ala Trp Thr Val Leu Leu Gly Pro Leu Gln Leu Cys
1               5                   10                  15

Ala Leu Val His Cys Ala Pro Pro Ala Gly Gln Gln Gln Pro Pro
                20                  25                  30

Arg Glu Pro Pro Ala Ala Pro Gly Ala Trp Arg Gln Gln Ile Gln Trp
            35                  40                  45

Glu Asn Asn Gly Gln Val Phe Ser Leu Leu Ser Leu Gly Ser Gln Tyr
            50                  55                  60

Gln Pro Gln Arg Arg Asp Pro Gly Ala Ala Val Pro Gly Ala Ala
65                  70                  75                  80

Asn Ala Ser Ala Gln Gln Pro Arg Thr Pro Ile Leu Leu Ile Arg Asp
                85                  90                  95

Asn Arg Thr Ala Ala Ala Arg Thr Arg Thr Ala Gly Ser Ser Gly Val
                100                 105                 110

Thr Ala Gly Arg Pro Arg Pro Thr Ala Arg His Trp Phe Gln Ala Gly
            115                 120                 125

Tyr Ser Thr Ser Arg Ala Arg Glu Arg Gly Ala Ser Arg Ala Glu Asn
        130                 135                 140

Gln Thr Ala Pro Gly Glu Val Pro Ala Leu Ser Asn Leu Arg Pro Pro
145                 150                 155                 160

Ser Arg Val Asp Gly Met Val Gly Asp Asp Pro Tyr Asn Pro Tyr Lys
                165                 170                 175

Tyr Ser Asp Asp Asn Pro Tyr Tyr Asn Tyr Tyr Asp Thr Tyr Glu Arg
                180                 185                 190

Pro Arg Pro Gly Gly Arg Tyr Arg Pro Gly Tyr Gly Thr Gly Tyr Phe
            195                 200                 205

Gln Tyr Gly Leu Pro Asp Leu Val Ala Asp Pro Tyr Tyr Ile Gln Ala
    210                 215                 220

Ser Thr Tyr Val Gln Lys Met Ser Met Tyr Asn Leu Arg Cys Ala Ala
225                 230                 235                 240

Glu Glu Asn Cys Leu Ala Ser Thr Ala Tyr Arg Ala Asp Val Arg Asp
                245                 250                 255

Tyr Asp His Arg Val Leu Leu Arg Phe Pro Gln Arg Val Lys Asn Gln
                260                 265                 270

Gly Thr Ser Asp Phe Leu Pro Ser Arg Pro Arg Tyr Ser Trp Glu Trp
            275                 280                 285

His Ser Cys His Gln His Tyr His Ser Met Asp Glu Phe Ser His Tyr
        290                 295                 300

Asp Leu Leu Asp Ala Asn Thr Gln Arg Arg Val Ala Glu Gly His Lys
305                 310                 315                 320

Ala Ser Phe Cys Leu Glu Asp Thr Ser Cys Asp Tyr Gly Tyr His Arg
                325                 330                 335

Arg Phe Ala Cys Thr Ala His Thr Gln Gly Leu Ser Pro Gly Cys Tyr
                340                 345                 350

Asp Thr Tyr Gly Ala Asp Ile Asp Cys Gln Trp Ile Asp Ile Thr Asp
            355                 360                 365
```

-continued

```
Val Lys Pro Gly Asn Tyr Ile Leu Lys Val Ser Val Asn Pro Ser Tyr
    370                 375                 380

Leu Val Pro Glu Ser Asp Tyr Thr Asn Val Val Arg Cys Asp Ile
385                 390                 395                 400

Arg Tyr Thr Gly His His Ala Tyr Ala Ser Gly Cys Thr Ile Ser Pro
                    405                 410                 415

Tyr

<210> SEQ ID NO 2
<211> LENGTH: 778
<212> TYPE: PRT
<213> ORGANISM: Homo sapiens

<400> SEQUENCE: 2

Met Ala Gln Lys Met Asp Cys Gly Ala Gly Leu Leu Gly Phe Gln Ala
1               5                   10                  15

Glu Ala Ser Val Glu Asp Ser Ala Leu Leu Met Gln Thr Leu Met Glu
                20                  25                  30

Ala Ile Gln Ile Ser Glu Ala Pro Pro Thr Asn Gln Ala Thr Ala Ala
            35                  40                  45

Ala Ser Pro Gln Ser Ser Gln Pro Pro Thr Ala Asn Glu Met Ala Asp
        50                  55                  60

Ile Gln Val Ser Ala Ala Ala Arg Pro Lys Ser Ala Phe Lys Val
65                  70                  75                  80

Gln Asn Ala Thr Thr Lys Gly Pro Asn Gly Val Tyr Asp Phe Ser Gln
                85                  90                  95

Ala His Asn Ala Lys Asp Val Pro Asn Thr Gln Pro Lys Ala Ala Phe
            100                 105                 110

Lys Ser Gln Asn Ala Thr Ser Lys Gly Pro Asn Ala Ala Tyr Asp Phe
        115                 120                 125

Ser Gln Ala Ala Thr Thr Gly Glu Leu Ala Ala Asn Lys Ser Glu Met
130                 135                 140

Ala Phe Lys Ala Gln Asn Ala Thr Thr Lys Val Gly Pro Asn Ala Thr
145                 150                 155                 160

Tyr Asn Phe Ser Gln Ser Leu Asn Ala Asn Asp Leu Ala Asn Ser Arg
                165                 170                 175

Pro Lys Thr Pro Phe Lys Ala Trp Asn Asp Thr Thr Lys Ala Pro Thr
            180                 185                 190

Ala Asp Thr Gln Thr Gln Asn Val Asn Gln Ala Lys Met Ala Thr Ser
        195                 200                 205

Gln Ala Asp Ile Glu Thr Asp Pro Gly Ile Ser Glu Pro Asp Gly Ala
210                 215                 220

Thr Ala Gln Thr Ser Ala Asp Gly Ser Gln Ala Gln Asn Leu Glu Ser
225                 230                 235                 240

Arg Thr Ile Ile Arg Gly Lys Arg Thr Arg Lys Ile Asn Asn Leu Asn
                245                 250                 255

Val Glu Glu Asn Ser Ser Gly Asp Gln Arg Arg Ala Pro Leu Ala Ala
            260                 265                 270

Gly Thr Trp Arg Ser Ala Pro Val Pro Val Thr Thr Gln Asn Pro Pro
        275                 280                 285

Gly Ala Pro Pro Asn Val Leu Trp Gln Thr Pro Leu Ala Trp Gln Asn
290                 295                 300

Pro Ser Gly Trp Gln Asn Gln Thr Ala Arg Gln Thr Pro Pro Ala Arg
305                 310                 315                 320
```

```
Gln Ser Pro Pro Ala Arg Gln Thr Pro Pro Ala Trp Gln Asn Pro Val
            325                 330                 335

Ala Trp Gln Asn Pro Val Ile Trp Pro Asn Pro Val Ile Trp Gln Asn
        340                 345                 350

Pro Val Ile Trp Pro Asn Pro Ile Val Trp Pro Gly Pro Val Val Trp
            355                 360                 365

Pro Asn Pro Leu Ala Trp Gln Asn Pro Pro Gly Trp Gln Thr Pro Pro
370                 375                 380

Gly Trp Gln Thr Pro Pro Gly Trp Gln Gly Pro Pro Asp Trp Gln Gly
385                 390                 395                 400

Pro Pro Asp Trp Pro Leu Pro Pro Asp Trp Pro Leu Pro Pro Asp Trp
                405                 410                 415

Pro Leu Pro Thr Asp Trp Pro Leu Pro Pro Asp Trp Ile Pro Ala Asp
                420                 425                 430

Trp Pro Ile Pro Pro Asp Trp Gln Asn Leu Arg Pro Ser Pro Asn Leu
        435                 440                 445

Arg Pro Ser Pro Asn Ser Arg Ala Ser Gln Asn Pro Gly Ala Ala Gln
        450                 455                 460

Pro Arg Asp Val Ala Leu Leu Gln Glu Arg Ala Asn Lys Leu Val Lys
465                 470                 475                 480

Tyr Leu Met Leu Lys Asp Tyr Thr Lys Val Pro Ile Lys Arg Ser Glu
                485                 490                 495

Met Leu Arg Asp Ile Ile Arg Glu Tyr Thr Asp Val Tyr Pro Glu Ile
                500                 505                 510

Ile Glu Arg Ala Cys Phe Val Leu Glu Lys Lys Phe Gly Ile Gln Leu
                515                 520                 525

Lys Glu Ile Asp Lys Glu Glu His Leu Tyr Ile Leu Ile Ser Thr Pro
            530                 535                 540

Glu Ser Leu Ala Gly Ile Leu Gly Thr Thr Lys Asp Thr Pro Lys Leu
545                 550                 555                 560

Gly Leu Leu Leu Val Ile Leu Gly Val Ile Phe Met Asn Gly Asn Arg
                565                 570                 575

Ala Ser Glu Ala Val Leu Trp Glu Ala Leu Arg Lys Met Gly Leu Arg
            580                 585                 590

Pro Gly Val Arg His Pro Leu Leu Gly Asp Leu Arg Lys Leu Leu Thr
            595                 600                 605

Tyr Glu Phe Val Lys Gln Lys Tyr Leu Asp Tyr Arg Arg Val Pro Asn
            610                 615                 620

Ser Asn Pro Pro Glu Tyr Glu Phe Leu Trp Gly Leu Arg Ser Tyr His
625                 630                 635                 640

Glu Thr Ser Lys Met Lys Val Leu Arg Phe Ile Ala Glu Val Gln Lys
                645                 650                 655

Arg Asp Pro Arg Asp Trp Thr Ala Gln Phe Met Glu Ala Ala Asp Glu
                660                 665                 670

Ala Leu Asp Ala Leu Asp Ala Ala Ala Glu Ala Glu Ala Arg Ala
            675                 680                 685

Glu Ala Arg Thr Arg Met Gly Ile Gly Asp Glu Ala Val Ser Gly Pro
            690                 695                 700

Trp Ser Trp Asp Asp Ile Glu Phe Glu Leu Leu Thr Trp Asp Glu Glu
705                 710                 715                 720

Gly Asp Phe Gly Asp Pro Trp Ser Arg Ile Pro Phe Thr Phe Trp Ala
                725                 730                 735
```

Arg Tyr His Gln Asn Ala Arg Ser Arg Phe Pro Gln Thr Phe Ala Gly
                740                 745                 750

Pro Ile Ile Gly Pro Gly Gly Thr Ala Ser Ala Asn Phe Ala Ala Asn
        755                 760                 765

Phe Gly Ala Ile Gly Phe Phe Trp Val Glu
    770                 775

<210> SEQ ID NO 3
<211> LENGTH: 1254
<212> TYPE: DNA
<213> ORGANISM: Homo sapiens

<400> SEQUENCE: 3

| | | | | | |
|---|---|---|---|---|---|
| atgcgcttcg | cctggaccgt | gctcctgctc | gggcctttgc | agctctgcgc | gctagtgcac | 60 |
| tgcgcccctc | ccgccgccgg | ccaacagcag | ccccgcgcg | agccgccggc | ggctccgggc | 120 |
| gcctggcgcc | agcagatcca | atgggagaac | aacgggcagg | tgttcagctt | gctgagcctg | 180 |
| ggctcacagt | accagcctca | cgccgccgg | gacccgggcg | ccgccgtccc | tggtgcagcc | 240 |
| aacgcctccg | cccagcagcc | ccgcactccg | atcctgctga | tccgcgacaa | ccgcaccgcc | 300 |
| gcggcgcgaa | cgcggacggc | cggctcatct | ggagtcaccg | ctggccgccc | caggcccacc | 360 |
| gcccgtcact | ggttccaagc | tggctactcg | acatctagag | cccgcgaacg | tggcgcctcg | 420 |
| cgcgcggaga | accagacagc | gccgggagaa | gttcctgcgc | tcagtaacct | gcggccgccc | 480 |
| agccgcgtgg | acggcatggt | gggcgacgac | ccttacaacc | cctacaagta | ctctgacgac | 540 |
| aacccttatt | acaactacta | cgatacttat | gaaaggccca | gacctggggg | caggtaccgg | 600 |
| cccggatacg | gcactggcta | cttccagtac | ggtctcccag | acctggtggc | cgacccctac | 660 |
| tacatccagg | cgtccacgta | cgtgcagaag | atgtccatgt | acaacctgag | atgcgcggcg | 720 |
| gaggaaaact | gtctggccag | tacagcatac | agggcagatg | tcagagatta | tgatcacagg | 780 |
| gtgctgctca | gatttcccca | aagagtgaaa | accaaggga | catcagattt | cttacccagc | 840 |
| cgaccaagat | attcctggga | atggcacagt | tgtcatcaac | attaccacag | tatggatgag | 900 |
| tttagccact | atgacctgct | tgatgccaac | acccagagga | gagtggctga | aggccacaaa | 960 |
| gcaagtttct | gtcttgaaga | cacatcctgt | gactatggc | accacaggcg | atttgcatgt | 1020 |
| actgcacaca | cacagggatt | gagtcctggc | tgttatgata | cctatggtgc | agacatagac | 1080 |
| tgccagtgga | ttgatattac | agatgtaaaa | cctggaaact | atatcctaaa | ggtcagtgta | 1140 |
| aaccccagct | acctggttcc | tgaatctgac | ataccaaca | atgttgtgcg | ctgtgacatt | 1200 |
| cgctacacag | gacatcatgc | gtatgcctca | ggctgcacaa | tttcaccgta | ttag | 1254 |

<210> SEQ ID NO 4
<211> LENGTH: 2713
<212> TYPE: DNA
<213> ORGANISM: Homo sapiens

<400> SEQUENCE: 4

| | | | | | |
|---|---|---|---|---|---|
| ggcacgagga | gagtgcggct | gctgagagcc | gagcccagca | atcccgatcc | tctgagtcgt | 60 |
| gaagaaggga | ggcagcgagg | gggttggggt | tggggcctga | ggcaagcccc | caggctccgc | 120 |
| tcttgccaga | gggacaggag | ccatggctca | gaaaatggac | tgtggtgcgg | gcctcctcgg | 180 |
| cttccaggct | gaggcctccg | tagaagacag | cgccttgctt | atgcagacct | tgatggaggc | 240 |
| catccagatc | tcagaggctc | cacctactaa | ccaggccacc | gcagctgcta | gtccccagag | 300 |
| ttcacagccc | ccaactgcca | atgagatggc | tgacattcag | gtttcagcag | ctgccgctag | 360 |

-continued

```
gcctaagtca gcctttaaag tccagaatgc caccacaaaa ggcccaaatg gtgtctatga      420
tttctctcag gctcataatg ccaaggatgt gcccaacacg cagcccaagg cagcctttaa      480
gtcccaaaat gctacctcca aaggtccaaa tgctgcctat gattttttccc aggcagcaac     540 cactggtgag ttagctgcta caagtctga gatggccttc aaggcccaga atgccactac       600
taaagtgggc ccaaatgcca cctacaattt ctctcagtct ctcaatgcca atgacctggc      660
caacagcagg cctaagaccc cttttcaaggc ttggaatgat accactaagg ccccaacagc    720
tgatacccag acccagaatg taaatcaggc caaaatggcc acttcccagg ctgacataga     780
gaccgaccca ggtatctctg aacctgacgg tgcaactgca cagacatcag cagatggttc     840
ccaggctcag aatctggagt cccggacaat aattcggggc aagaggaccc gcaagattaa     900
taacttgaat gttgaagaga cagcagtggg ggatcagagg cgggcccac tggctgcagg      960 gacctggagg tctgcaccag ttccagtgac cactcagaac ccacctggcg caccccccaa    1020
tgtgctctgg cagacgccat ggcttggca gaacccctca ggctggcaaa accagacagc    1080
caggcagacc ccaccagcac gtcagagccc tccagctagg cagaccccac cagcctggca    1140
gaacccagtc gcttggcaga acccagtgat ttggccaaac ccagtaatct ggcagaaccc    1200
agtgatctgg ccaaaccccca ttgtctggcc cggccctgtt gtctggccga atccactggc    1260
ctggcagaat ccacctggat ggcagactcc acctggatgg cagaccccac cgggctggca    1320
gggtcctcca gactggcaag gtcctcctga ctggccgcta ccacccgact ggccactgcc    1380
acctgattgg ccacttccca ctgactggcc actaccacct gactggatcc ccgctgattg    1440
gccaattcca cctgactggc agaacctgcg cccctcgcct aacctgcgcc cttctcccaa    1500
ctcgcgtgcc tcacagaacc caggtgctgc acagccccga gatgtggccc ttcttcagga    1560
aagagcaaat aagttggtca agtacttgat gcttaaggac tacacaaagg tgcccatcaa    1620
gcgctcagaa atgctgagag atatcatccg tgaatacact gatgtttatc cagaaatcat    1680
tgaacgtgca tgctttttgtcc tagagaagaa atttgggatt caactgaaag aaattgacaa    1740
agaagaacac ctgtatattc tcatcagtac ccccgagtcc ctggctggca tactgggaac    1800
gaccaaagac acacccaagc tcggtctcct cttggtgatt ctgggtgtca tcttcatgaa    1860
tggcaaccgt gccagtgagg ctgtcctctg ggaggcacta cgcaagatgg gactgcgtcc    1920
tggggtgaga catcccctcc ttggagatct aaggaaactt ctcacctatg agtttgtaaa    1980
gcagaaatac ctggactaca gacgagtgcc caacagcaac ccccggagt atgagttcct     2040 ctggggcctc cgttcctacc atgagactag caagatgaaa gtgctgagat tcattgcaga    2100
ggttcagaaa agagaccctc gtgactggac tgcacagttc atggaggctg cagatgaggc    2160
cttggatgct ctggatgctg ctgcagctga ggccgaagcc cgggctgaag caagaacccg    2220
catgggaatt ggagatgagg ctgtgtctgg gccctggagc tgggatgaca ttgagtttga    2280
gctgctgacc tgggatgagg aaggagattt tggagatccc tggtccagaa ttccatttac    2340
cttctgggcc agataccacc agaatgcccg ctccagattc cctcagacct tgccggtcc     2400 cattattggt cctggtggta cagccagtgc caacttcgct gccaactttg gtgccattgg    2460
tttcttctgg gttgagtgag atgttggata ttgctatcaa tcgcagtagt ctttcccctg    2520
tgtgagctga agcctcagat tccttctaaa cacagctatc tagagagcca catcctgttg    2580
actgaaagtg gcatgcaaga taaatttatt tgctgttcct tgtctactgc ttttttttccc   2640
```

```
cttgtgtgct gtcaagtttt ggtatcagaa ataaacattg aaattgcaaa gtgaaaaaaa    2700
aaaaaaaaaa aaa                                                      2713
```